United States Patent
Jonas et al.

[11] Patent Number: 6,130,223
[45] Date of Patent: Oct. 10, 2000

[54] THIENOPYRIMIDINE WITH PHOSPHODIESTERASE V INHIBITING EFFECT

[75] Inventors: Rochus Jonas, Stormstrasse; Pierre Schelling, Mühltal; Maria Christadler, Rödermark; Franz-Werner Kluxen, Darmstadt, all of Germany

[73] Assignee: Merck Patent Gesellschaft mit beschrankter Haftung, Germany

[21] Appl. No.: 09/297,186

[22] PCT Filed: Oct. 8, 1997

[86] PCT No.: PCT/EP97/05530

§ 371 Date: Jun. 11, 1999

§ 102(e) Date: Jun. 11, 1999

[87] PCT Pub. No.: WO98/17668

PCT Pub. Date: Apr. 30, 1998

[30] Foreign Application Priority Data

Oct. 24, 1996 [DE] Germany ............ 196 44 228

[51] Int. Cl.[7] ............ A61R 31/519; C07D 495/04
[52] U.S. Cl. ............ 514/258; 544/278
[58] Field of Search ............ 544/278; 514/258

[56] References Cited

U.S. PATENT DOCUMENTS

| | | | |
|---|---|---|---|
| 4,666,908 | 5/1987 | Hamilton | 544/262 |
| 5,075,310 | 12/1991 | Coalis et al. | 544/254 |
| 5,436,233 | 7/1995 | Lee et al. | 544/284 |
| 5,525,604 | 6/1996 | Lee et al. | 544/324 |
| 5,693,652 | 12/1997 | Takase et al. | 548/305.1 |
| 5,707,998 | 1/1998 | Takase et al. | 544/283 |
| 5,869,486 | 2/1999 | Lee et al. | 544/278 |

FOREIGN PATENT DOCUMENTS

| | | |
|---|---|---|
| 0 201 188 | 12/1986 | European Pat. Off. . |
| 0 349 239 | 1/1990 | European Pat. Off. . |
| 0 579 496 | 1/1994 | European Pat. Off. . |
| 0 607 439 | 7/1994 | European Pat. Off. . |
| 0 640 599 | 3/1995 | European Pat. Off. . |
| 0 728 759 | 8/1996 | European Pat. Off. . |
| 94 22858 | 10/1994 | WIPO . |

OTHER PUBLICATIONS

Lee et al. J. Med. Chem. 38, 3547–3557., 1995.
Takase et al. J. Med. Chem. 37, 2106–2127, 1994.
Takase et al. J. Med . Chem. 36, 3765–3770, 1993.

*Primary Examiner*—Richard L. Raymond
*Assistant Examiner*—V Balasubramanian
*Attorney, Agent, or Firm*—Millen, White, Zelano & Branigan, P.C.

[57] ABSTRACT

The invention relates to thienopyrimidine of the formula (I) as well as to their physiologically acceptable salts, wherein $R^1$, $R^2$, $R^3$, $R^4$, X and n have the meaning cited in claim 1. Said compounds exhibit a phosphodiesterase V inhibition and can be used in the treatment of cardiovascular dieases and for the treatment and/or therapy potency disorder.

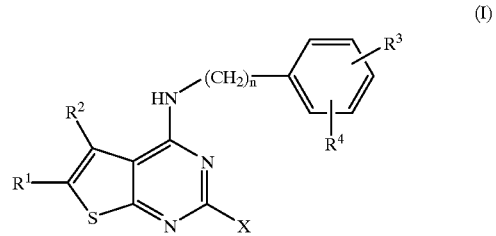

(I)

8 Claims, No Drawings

THIENOPYRIMIDINE WITH PHOSPHODIESTERASE V INHIBITING EFFECT

This application is a 371 of PCT/EP97/05539, filed Oct. 8, 1997.

The invention relates to compounds of the formula I

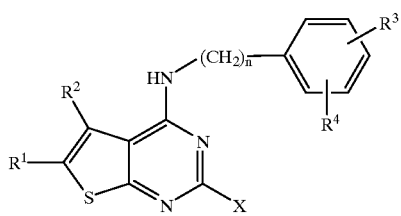

wherein $R^1$, $R^2$ in each case independently of one another are H, A, OA, alkenyl, alkynyl, $CR_3$ or Hal, wherein one of the radicals R or $R^2$ is always ≠H, $R^1$ and $R^2$ together are also alkylene having 3–5 C atoms, $R^3$, $R^4$ in each case independently of one another are H, A, OA, $NO_2$, $NH_2$ NHA, NAA' or Hal, $R^3$ and $R^4$ together also are —O—$CH_2$—$CH_2$—, —O—$CH_2$—O— or —O—$CH_2$—$CH_2$—O—, X is a 5- to 7-membered saturated heterocyclic ring which is mono- or disubstituted by $R^5$, or a 5- to 7-membered unsaturated or saturated isocyclic ring which is mono- or disubstituted by $R^5$, $R^5$ is COOH, COOA, $CONH_2$, CONAA', CONHA, CN, $CH_2COOH$ or $CH_2CH_2COOH$, A,A' in each case independently of one another are H or alkyl having 1 to 6 C atoms, Hal is F, Cl, Br or I and n is 0, 1, 2 or 3, and physiologically acceptable salts thereof.

Pyrimidine derivatives are known, for example, from EP 201 188 or WO 93/06104.

The invention was based on the object of discovering new compounds having valuable properties, in particular those which can be used for the preparation of medicaments.

It has been found that the compounds of the formula I and their salts have very valuable pharmacological properties, coupled with a good tolerability.

In particular, they exhibit specific inhibition of cGMP-phosphodiesterase (PDE V).

Quinazolines having an inhibitory activity with regard to cGMP-phosphodiesterase are described, for example, in J.Med. Chem. 36, 3765 (1993) and ibid. 37, 2106 (1994).

The biological activity of the compounds of the formula I can be determined by methods such as are described, for example, in WO 93/06104. The affinity of the compounds according to the invention for cGMP- and cAMP-phosphodiesterase is ascertained by determining their $IC_{50}$ values (concentration of the inhibitor required to achieve a 50% inhibition of the enzyme activity).

Enzymes isolated by known methods can be used for carrying out the determinations (for example W. J. Thompson et al., Biochem. 1971, 10, 311). A modified "batch" method of W. J. Thompson and M. M. Appleman (Biochem. 1979, 18, 5228) can be used for carrying out the experiments.

The compounds are therefore suitable for the treatment of diseases of the cardiovascular system, in particular cardiac insufficiency, and for treatment and/or therapy of disturbances in potency (erectile dysfunction).

The use of substituted pyrazolopyrimidinones for treating impotence is described, for example, in WO 94/28902.

The compounds are effective as inhibitors of phenylephrine-induced contractions in corpus cavernosum preparations of hares.

This biological action can be detected, for example, by the method described by F Holmauist et al. in J.Urol., 150, 1310–1315 (1993).

The inhibition of the contraction demonstrates the activity of the compounds according to the invention for therapy and/or treatment of disturbances in potency.

The compounds of the formula I can be employed as medicament active compounds in human and veterinary medicine. They can furthermore be employed as intermediate products for the preparation of further medicament active compounds.

The invention accordingly relates to the compounds of the formula I and a process for the preparation a) of compounds of the formula I according to claim 1, and salts thereof, wherein X is a saturated 5- to 7-membered heterocyclic ring which is mono- or disubstituted by $R^5$ and is bonded via N, characterized in that a compound of the formula II

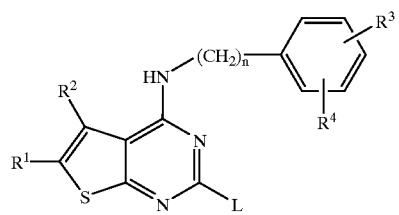

wherein $R^1$, $R^2$, $R^3$, $R^4$ and n have the meanings given and L is Cl, Br, OH, $SCH_3$ or a reactive esterified OH group, is reacted with a saturated 5- to 7-membered heterocyclic ring which is mono- or disubstituted by $R^5$, wherein $R^5$ has the meaning given, or b) of compounds of the formula I according to claim 1, and salts thereof, wherein X is an unsaturated or saturated 5- to 7-membered isocyclic ring which is mono- or disubstituted by $R^5$ and is bonded via C, characterized in that a compound of the formula III

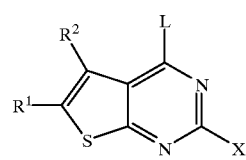

wherein $R^1$, $R^2$ and X have the meanings given and L is Cl, Br, OH, $SCH_3$ or a reactive esterified OH group, is reacted with a compound of the formula IV

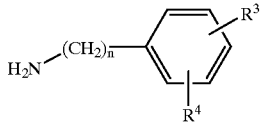

IV wherein $R^3$, $R^4$ and n have the meanings given, or c) in a compound of the formula I a radical $R^3$, $R^4$ and/or X is converted into another radical $R^3$, $R^4$ and/or X by hydrolysing an ester or reducing a nitro group, and/or in that an acid compound of the formula I is converted into one of its salts by treatment with a base.

The radicals $R^1$, $R^2$, $R^3$, $R^4$, X, L and n above and below have the meanings given in1 the case of the formulae I, II, III, IV and V, unless expressly stated otherwise.

A and A' are preferably in each case independently of one another alkyl having 1–6 C atoms.

In the above formulae, alkyl is preferably unbranched and has 1, 2, 3, 4, 5 or 6 C atoms, preferably 1, 2, 3, 4 or 5 C atoms, and is preferably methyl, ethyl or propyl, or furthermore preferably isopropyl, butyl, isobutyl, sec-butyl or tert-butyl, or also n-pentyl, neopentyl or isopentyl.

Alkylene is preferably unbranched and is preferably propylene, butylene or pentylene.

Of the radicals $R^1$ and $R^2$, one is preferably H, while the other is preferably propyl or butyl, but particularly preferably ethyl or methyl. Furthermore, $R^1$ and $R^2$ together are also preferably propylene, butylene or pentylene.

Hal is preferably F, Cl or Br, or else I.

Alkenyl is preferably vinyl, 1- or 2-propenyl, 1-butenyl, isobutenyl or sec-butenyl, and 1-pentenyl, iso-pentenyl or 1-hexenyl are furthermore preferred.

Alkynyl is preferably ethynyl or propyn-1-yl, or furthermore butyn-1- or butyn-2-yl or pentyn-1-, pentyn-2- or pentyn-3-yl.

The radicals $R^3$ and $R^4$ can be identical or different and are preferably in the 3- or 4-position of the phenyl ring. They are, for example, in each case independently of one another H, alkyl, alkoxy, nitro, amino, alkylamino, such as, for example methylamino, dialkylamino, such as, for example, dimethylamino, F, Cl, Br or I, or together ethyleneoxy, methylenedioxy, or ethylenedioxy. They are preferably also in each case alkoxy, such as, for example, methoxy, ethoxy or propoxy.

The radical $R^5$ is preferably, for example COOH, $COOCH_3$, $COOC_2H_5$, $CONH_2$, $CON(CH_3)_2$ $CONHCH_3$, CN, $CH_2COOH$ or $CH_2CH_2COOH$.

The radical X is preferably phenyl, cyclopentyl, cyclohexyl, cycloheptyl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1, -2-, -3-, -4-, or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4- -5- or -6-pyridyl, 1-, 2- 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, 6-, -7- or -8-quinolyl, 1,2,3,4-tetrahydro-1-, -2-, -3-, -4-, -5-, -6-, -7- or -8-isoquinolyl which are mono- or disubstituted by COOH, $COOCH_3$, $COOC_2H_5$, $CONH_2$, $CON(CH_3)_2$, $CONHCH_3$ or CN.

For the entire invention, all the radicals which occur several times can be identical or different, that is to say independent of one another.

The invention accordingly particularly relates to those compounds of the formula I in which at least one of the radicals mentioned has one of the abovementioned preferred meanings. Some preferred groups of compounds can be expressed by the following part formulae 1a to 1e, which correspond to the formula I and wherein the radicals not defined in more detail have the meaning given in the case of the formula I, but wherein in Ia X is phenyl, 1-piperidinyl or cyclohexyl which are mono- or disubstituted by COOH, COOA, $CONH_2$, CONAA', CONHA, CN, $CH_2COOH$ or $CH_2CH_2COOH$;

in Ib $R^1$, $R^2$ in each case independently of one another are H, A, OA, $NO_2$, CFB or Hal, wherein at least one of the radicals $R^1$ or $R^2$ is always ≠H, $R^3$ and $R^4$ together are $-O-CH_2-CH_2-$, $-O-CH_2-O-$ or $-O-CH_2-CH_2O$, X is phenyl, 1-piperidinyl or cyclohexyl which are mono- or disubstituted by COOH, COOA, $CONH_2$, CONAA', CONHA, CN, $CH_2COOH$ or $CH_2CH_2COOH$ and n is 1;

in Ic $R^1$, $R^2$ in each case independently of one another are H, A, OA, $NO_2$, $CF_3$ or Hal, wherein at least one of the radicals $R^1$ or $R^2$ is always ≠H, $R^3$, $R^4$ in each case independently of one another are H, A, OA, Hal, $NO_2$, $NHO_2$, NHA or NAA', X is phenyl, 1-piperidinyl or cyclohexyl which are mono- or disubstituted by COOH, COOA, $CONH_2$, CONAA', CONHA, CN, $CH_2COOH$ or $CH_2CH_2COOH$ and n is 1;

in Id $R^1$ and $R^2$ together are alkylene having 3–5 C atoms, $R^3$ and $R^4$ together are $-O-CH_2-CH_2-$, $-O-CH_2-O-$ or $-O-CH_2-CH_2-O$, X is phenyl, 1-piperidinyl or cyclohexyl which are mono- or disubstituted by COOH, COOA, $CONH_2$, CONAA', CONHA, CN, $CH_2COOH$ or $CH_2CH_2COOH$ and n is 1;

in Ie $R^1$ and $R^2$ together are alkylene having 3–5 C atoms, $R^3$, $R^4$ in each case independently of one another are H, A, OA, Hal, $NO_2$, $NH_2$, NHA or NAA', X is phenyl, 1-piperidinyl or cyclohexyl which are mono- or disubstituted by COOH, COOA, $CONH_2$, CONAA', CONHA, CN, $CH_2COOH$ or $CH_2CH_2COOH$ and n is 1.

The compounds of the formula I and also the starting substances for their preparation are otherwise prepared by methods known per se, such as are described in the literature (for example in the standard works, such as Houben-Weyl, Methoden der organischen Chemie [Methods of Organic Chemistry], Georg-Thieme-Verlag, Stuttgart), and in particular under reaction conditions which are known and suitable for the reactions mentioned. For these reactions, it is also possible to utilize variants which are known per se and are not mentioned here in more detail.

In the compounds of the formulae II, III and IV, $R^1$, $R^2$, $R^3$, $R^4$, X and n have the meanings given, in particular the preferred meanings given.

If L is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy, or futhermore also 2-naphthalenesulfonyloxy).

If desired, the starting substances can also be formed in situ, so that they are not isolated from the reaction mixture but are immediately reacted further to give the compounds of the formula I.

On the other hand, it is possible to carry out the reaction in stages.

The compounds of the formula I in which X is bonded to the thienopyrimidine ring system via N can preferably be obtained by reacting compounds of the formula II with a saturated 5- to 7-membered heterocyclic ring which is unsubstituted or mono- or disubstituted by COOH, COOA, $CONH_2$, CONAA', CONHA or CN.

The starting substances of the formula II are known in some cases. If they are not known, they can be prepared by methods known per se.

Precursors of the compounds of the formula II can be prepared, for example, by cyclization and halogenation analogously to J. Med. Chem. 24, 374 (1981). The compounds of the formula II are obtained by subsequent reaction with arylalkylamines.

In detail, the reaction of the compounds of the formula II with the NH-containing heterocyclic ring is carried out in the presence or absence of an inert solvent at temperatures between about –20 and about 150°, preferably between 20 and 100°.

The addition of an acid-binding agent, for example an alkali metal hydroxide, carbonate or bicarbonate or alkaline earth metal hydroxide, carbonate or bicarbonate, or of an alkali metal or alkaline earth metal, preferably potassium, sodium or calcium, salt of a weak acid, or the addition of an organic base, such as triethylamine, dimethylamine, pyridine or quinoline, or of an excess of the amine component may be favourable.

Suitable inert solvents are for example hydrocarbons, such as hexane, petroleum ether, benzene, toluene or xylene; chlorinated hydrocarbons, such as trichloroethylene, 1,2-dichloroethane, carbon tetrachloride, chloroform or methylene chloride; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether (methylglycol or ethylglycol) or ethylene glycol dimethyl ether (diglyme); ketones, such as acetone or butanone; amides, such as acetaimide, dimethylacetamide or dimethylformamide (DMF); nitriles, such as acetonitrile; sulfoxides, such as dimethylsulfoxide (DMSO); nitro compounds, such as nitromethane or nitrobenzene; esters, such as ethyl acetate, or mixtures of the solvents mentioned.

Compounds of the formula I wherein X is bonded to the thienopyrimidine ring system via C can furthermore be obtained by reacting compounds of the formula III with compounds of the formula IV. The starting compounds of the formula IV and V are as a rule known. If they are not known, they can be prepared by methods known per se.

Compounds of the formula III can be obtained, for example, by reaction with $POCl_3$ of compounds which are built up from thiophene derivatives and CN-substituted isocyclic rings (Eur. J. Med. Chem. 23, 453 (1988).

The reaction of the compounds of the formula III with compounds of the formula IV is carried out under similar conditions regarding the reaction time, temperature and solvent as are described for the reaction of the compounds of the formula II with the NH-containing heterocyclic rings.

It is furthermore possible to convert a radical $R^3$ and/or $R^4$ in a compound of the formula I into another radical $R^3$ and/or $R^4$, for example by reducing nitro groups to amino groups (for example by hydrogenation over Raney nickel or Pd-on-charcoal in an inert solvent, such as methanol or ethanol) or hydrolysing cyano groups to COOH groups.

An acid of the formula I can be converted into the associated acid addition salt with a base, for example by reaction of equivalent amounts of the acid and the base in an inert solvent, such as ethanol, and subsequent evaporation. Possible bases for this reaction are, in particular, those which give physiologically acceptable salts.

The acid of the formula I can thus be converted with a base (for example sodium hydroxide or carbonate or potassium hydroxide or carbonate) into the corresponding metal salt, in particular alkali metal or alkaline earth metal salt, or into the corresponding ammonium salt.

On the other hand, a base of the formula I can be converted into the associated acid addition salt with an acid, for example by reaction of equivalent amounts of the base and the acid in an inert solvent, such as ethanol, and subsequent evaporation. Acids which are possible for this reaction are, in particular, those which give physiologically acceptable salts. It is thus possible to use inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, glyconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and laurylsulfuric acid. Salts with physiologically unacceptable acids, for example picrates, can be used for isolation and/or purification of the compounds of the formula I. The invention furthermore relates to the use of the compounds of the formula I and/or of their physiologically acceptable salts for the preparation of pharmaceutical formulations, in particular by a non-chemical route. For this use, they can be brought into a suitable dosage form together with at least one solid, liquid and/or semi-solid carrier or auxiliary, and if appropriate in combination with one or more further active compounds.

The invention also relates to medicaments of the formula I and their physiologically acceptable salts as phosphodiesterase V inhibitors.

The invention furthermore relates to pharmaceutical formulations comprising at least one compound of the formula I and/or one of its physiologically acceptable salts.

These formulations can be used as medicaments in human or veterinary medicine. Possible carriers are organic or inorganic substances which are suitable for enteral (for example oral), parenteral or topical administration and do not react with the new compounds, for example water, vegetable oils, benzyl alcohols, alkylene glycols, polyethylene glycols, glycerol triacetate, gelatin, carbohydrates, such as lactose or starch, magnesium stearate, talc and vaseline. Tablets, pills, coated tablets, capsules, powders, granules, syrups, juices or drops are used, in particular, for oral administration, suppositories are used for rectal administration, solutions, preferably oily or aqueous solutions, and furthermore suspensions, emulsions or implants are used for parental administration, and ointments, creams or powders are used for topical application. The new compounds can also be lyophilized and the resulting lyophilizates can be used, for example, for the preparation of injection preparations. The formulations mentioned can be sterilized and/or comprise auxiliaries, such as lubricants, preservatives, stabilizers and/or wetting agents, emulsifiers, salts for influencing the osmotic pressure, buffer substances, dyestuffs, flavourings and/or several further active compounds, for example one or more vitamins.

The compounds of the formula I and their physiologically acceptable salts can be employed for combating diseases with which an increase in the cGMP (cyclo-guanosine monophosphate) level leads to an inhibition or prevention of inflammation and to muscular relaxation. The compounds according to the invention can be used in particular in the treatment of diseases of the cardiovascular system and for the treatment and/or therapy of disturbances in potency.

For these uses, the substances are as a rule preferably administered in dosages of between about 1 and 500 mg, in particular between 5 and 100 mg per dosage unit. The daily dosage is preferably between about 0.02 and 10 mg/kg of body weight. However, the specific dose for each patient depends on the most diverse factors, for example on the activity of the specific compound employed, on the age, body weight, general state of health and sex, on the diet, on the administration time and route, and on the rate of excretion, medicament combination and severity of the particular disease to which the therapy applies. Oral administration is preferred.

All the temperatures above and below are stated in ° C. In the following examples, "customary working up" means: water is added, if necessary, the pH is adjusted to between 2 and 10, if necessary, depending on the structure of the end product, the mixture is extracted with ethyl acetate or methylene chloride, the organic phase is separated off, dried over sodium sulfate and evaporated and the residue is purified by chromatography over silica gel and/or by crystallization.

Mass spectrometry (MS): EI (electron impact ionization) $M^+$ FAB (fast atom bombardment) $(M+H)^+$

EXAMPLE 1

3.02 g of 3,4-methylenedioxybenzylamine ("A") are added to a solution of 3.29 g of 2,4-dichloro-6-methylthieno-[2,3-d]-pyrimidine in 80 ml of methylene chloride and, after addition of 1.52 g of triethylamine, the mixture is stirred at room temperature for 12 hours. The solvent is removed and the residue is worked up in the customary manner. 3.38 g of 2-chloro-6-methyl-4-(3,4-methylenedioxybenzylamino)-thieno-[2,3-d]-pyrimidine are obtained, m.p. 162°.

Analogously, by reaction of "A"
with 2,4-dichloro-5-methyl-thieno-[2,3-d]-pyrimidine,
2-chloro-5-methyl-4-(3,4-methylenedioxybenzylamino)-thieno-[2,3-d] -pyrimidine;
with 2,4-dichloro-5,6,7,8-tetrahydro-[1]-benzothieno-[2,3-d]-pyrimidine,
2-chloro-5,6,7,8-tetrahydro-4-(3,4-methylenedioxybenzylamino)-[1]-benzothieno-[2,3-d]-pyrimidine, m.p. 222°;
with 2,4-dichloro-5,6-cyclopenteno-[1]-benzothieno-[2,3-d]-pyrimidine,
2-chloro-5,6-cyclopenteno-4-(3,4-methylenedioxybenzylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3,4-methylenedioxybenzylamino)-[1]-benzothieno-[2,3-d]-pyrimidine;
with 2,4-dichloro-6-ethyl-thieno-[2,3-d]-pyrimidine,
2-chloro-6-ethyl-4-(3,4-methylenedioxybenzylamino)-thieno-[2,3-d]-pyrimidine, m.p. 148°;
with 2,4,6-trichloro-thieno-[2,3-d]-pyrimidine,
2,6-dichloro-4-(3,4-methylenedioxybenzylamino)-thieno-[2,3-d]-pyrimidine;
with 2,4,5-trichloro-6-methyl-thieno-[2,3-d]-pyrimidine,
2,5-dichloro-6-methyl-4-(3,4-methylenedioxybenzylamino)-thieno-[2,3-d]-pyrimidine;
with 2,4-dichloro-6-nitro-thieno-[2,3-d]-pyrimidine,
2-chloro-6-nitro-4-(3,4-methylenedioxybenzylamino)-thieno-[2,3-d]-pyrimidine;
with 2,4-dichloro-5,6-dimethyl-thieno-[2,3-d]-pyrimidine,
2-chloro-5,6-dimethyl-4-(3,4-methylenedioxybenzylamino)-thieno-[2,3-d]-pyrimidine;
with 2,4-dichloro-6-trifluoromethyl-thieno-[2,3-d]-pyrimidine,
2-chloro-6-trifluoromethyl-4-(3,4-methylenedioxybenzylamino)-thieno-[2,3-d]-pyrimidine,
are obtained.

Analogously, by reaction of 3-chloro-4-methoxybenzylamine
with 2,4-dichloro-6-methyl-thieno-[2,3-d]-pyrimidine,
2-chloro-6-methyl-4-(3-chloro-4-methoxybenzylamino)-thieno-[2,3-d]-pyrimidine;
with 2,4-dichloro-5-methyl-thieno-[2,3-d]-pyrimidine,
2-chloro-5-methyl-4-(3-chloro-4-methoxybenzylamino)-thieno-[2,3-d]-pyrimidine;
with 2,4-dichloro-5,6,7,8-tetrahydro-[1]-benzothieno-[2,3-d]-pyrimidine,
2-chloro-5,6,7,8-tetrahydro-4-(3-chloro-4-methoxybenzylamino)-[1]-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-(3-chloro-4-methoxybenzylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3-chloro-4-methoxybenzylamino)-[1]-benzothieno-[2,3-d]-pyrimidine;
with 2,4-dichloro-6-ethyl-thieno-[2,3-d]-pyrimidine,
2-chloro-6-ethyl-4-(3-chloro-4-methoxybenzylamino)-thieno-[2,3-d]-pyrimidine;
with 2,4,6-trichloro-thieno-[2,3-d]-pyrimidine,
2,6-dichloro-4-(3-chloro-4-methoxybenzylamino)-thieno-[2,3-d]-pyrimidine;
with 2,4,5-trichloro-6-methyl-thieno-[2,3-d]-pyrimidine,
2,5-dichloro-6-methyl-4-(3-chloro-4-methoxybenzylamino)-thieno-[2,3-d]-pyrimidine;
with 2,4-dichloro-6-nitro-thieno-[2,3-d]-pyrimidine,
2-chloro-6-nitro-4-(3-chloro-4-methoxybenzylamino)-thieno-[2,3-d]-pyrimidine;
with 2,4-dichloro-5,6-dimethyl-thieno-[2,3-d]-pyrimidine,
2-chloro-5,6-dimethyl-4-(3-chloro-4-methoxybenzylamino)-thieno-[2,3-d]-pyrimidine;
with 2,4-dichloro-6-trifluoromethyl-thieno-[2,3-d]-pyrimidine,
2-chloro-6-trifluoromethyl-4-(3-chloro-4-methoxybenzylamino)-thieno-[2,3-d]-pyrimidine,
are obtained.

Analogously, by reaction of 3,4-dimethoxybenzylamine
with 2,4-dichloro-6-methyl-thieno-[2,3-d]-pyrimidine,
2-chloro-6-methyl-4-(3,4-dimethoxybenzylamino)-thieno-[2,3-d]-pyrimidine;

with 2,4-dichloro-5-methyl-thieno-[2,3-d]-pyrimidine,
2-chloro-6-methyl-4-(3,4-dimethoxybenzylamino)-thieno-[2,3-d]-pyrimidine;
with 2,4-dichloro-5,6,7,8-tetrahydro-[1]-[1]-benzothieno-[2,3-d]-pyrimidine,
2-chloro-5,6,7,8-tetrahydro-4-(3,4-dimethoxybenzylamino)-[1]-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-(3,4-dimethoxybenzylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3,4-dimethoxybenzylamino)-[1]-benzothieno-[2,3-d]-pyrimidine;
with 2,4-dichloro-6-ethyl-thieno-[2,3-d]-pyrimidine,
2-chloro-6-ethyl-4-(3,4-dimethoxybenzylamino)-thieno-[2,3-d]-pyrimidine;
with 2,4,6-trichloro-thieno-[2,3-d]-pyrimidine,
2,6-dichloro-4-(3,4-dimethoxybenzylamino)-thieno-[2,3-d]-pyrimidine;
with 2,4,5-trichloro-6-methyl-thieno-[2,3-d]-pyrimidine,
2,5-dichloro-6-methyl-4-(3,4-dimethoxybenzylamino)-thieno-[2,3-d]-pyrimidine;
with 2,4-dichloro-6-nitro-thieno-[2,3-d]-pyrimidine,
2-chloro-6-nitro-4-(3,4-dimethoxybenzylamino)-thieno-[2,3-d]-pyrimidine;
with 2,4-dichloro-5,6-dimethyl-thieno-[2,3-d]-pyrimidine,
2-chloro-5,6-dimethyl-4-(3,4-dimethoxybenzylamino)-thieno-[2,3-d]-pyrimidine;
with 2,4-dichloro-6-trifluoromethyl-thieno-[2,3-d]-pyrimidine,
2-chloro-6-trifluoromethyl-4-(3,4-dimethoxybenzylamino)-thieno-[2,3-d]-pyrimidine,
are obtained.

Analogously, by reaction of benzylamine
with 2,4-dichloro-6-methyl-thieno-[2,3-d]-pyrimidine,
2-chloro-6-methyl-4-benzylamino-thieno-[2,3-d]-pyrimidine;
with 2,4-dichloro-5-methyl-thieno-[2,3-d]-pyrimidine,
2-chloro-5-methyl-4-benzylamino-thieno-[2,3-d]-pyrimidine;
with 2,4-dichloro-5,6,7,8-tetrahydro-[1]-[1]-benzothieno-[2,3-d]-pyrimidine,
2-chloro-5,6,7,8-tetrahydro-4-benzylamino-[1]-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-benzylamino-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-benzylamino-[1]-benzothieno-[2,3-d]-pyrimidine;
with 2,4-dichloro-6-ethyl-thieno-[2,3-d]-pyrimidine,
2-chloro-6-ethyl-4-benzylamino-thieno-[2,3-d]-pyrimidine;
with 2,4,6-trichloro-thieno-[2,3-d]-pyrimidine,
2,6-dichloro-4-benzylamino-thieno-[2,3-d]-pyrimidine;
with 2,4,5-trichloro-6-methyl-thieno-[2,3-d]-pyrimidine,
2,5-dichloro-6-methyl-4-benzylamino-thieno-[2,3-d]-pyrimidine;
with 2,4-dichloro-6-nitro-thieno-[2,3-d]-pyrimidine,
2-chloro-6-nitro-4-benzylamino-thieno-[2,3-d]-pyrimidine;
with 2,4-dichloro-5,6-dimethyl-thieno-[2,3-d]-pyrimidine,
2-chloro-5,6-dimethyl-4-benzylamino-thieno-[2,3-d]-pyrimidine;
with 2,4-dichloro-6-trifluoromethyl-thieno-[2,3-d]-pyrimidine,
2-chloro-6-trifluoromethyl-4-benzylamino-thieno-[2,3-d]-pyrimidine,
are obtained.

Analogously, by reaction of 4-fluorobenzylamine
with 2,4-dichloro-6-methyl-thieno-[2,3-d]-pyrimidine,
2-chloro-6-methyl-4-(4-fluorobenzylamino)-thieno-[2,3-d]-pyrimidine;
with 2,4-dichloro-5-methyl-thieno-[2,3-d]-pyrimidine,
2-chloro-5-methyl-4-(4-fluorobenzylamino)-thieno-[2,3-d]-pyrimidine;
with 2,4-dichloro-5,6,7,8-tetrahydro-[1]-benzothieno-[2,3-d]-pyrimidine,
2-chloro-5,6,7,8-tetrahydro-4-(4-fluorobenzylamino)-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-(4-fluorobenzylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(4-fluorobenzylamino)-[1]-benzothieno-[2,3-d]-pyrimidine;
with 2,4-dichloro-6-ethyl-thieno-[2,3-d]-pyrimidine,
2-chloro-6-ethyl-4-(4-fluorobenzylamino)-thieno-[2,3-d]-pyrimidine;
with 2,4,6-trichloro-thieno-[2,3-d]-pyrimidine,
2,6-dichloro-4-(4-fluorobenzylamino)-thieno-[2,3-d]-pyrimidine;
with 2,4,5-trichloro-6-methyl-thieno-[2,3-d]-pyrimidine,
2,5-dichloro-6-methyl-4-(4-fluorobenzylamino)-thieno-[2,3-d]-pyrimidine;
with 2,4-dichloro-6-nitro-thieno-[2,3-d]-pyrimidine,
2-chloro-6-nitro-4-(4-fluorobenzylamino)-thieno-[2,3-d]-pyrimidine;
with 2,4-dichloro-5,6-dimethyl-thieno-[2,3-d]-pyrimidine,
2-chloro-5,6-dimethyl-4-(4-fluorobenzylamino)-thieno-[2,3-d]-pyrimidine;
with 2,4-dichloro-6-trifluoromethyl-thieno-[2,3-d]-pyrimidine,
2-chloro-6-trifluoromethyl-4-(4-fluorobenzylamino)-thieno-[2,3-d]-pyrimidine,
are obtained.

Analogously, by reaction of 3,4-dichlorobenzylamine
with 2,4-dichloro-6-methyl-thieno-[2,3-d]-pyrimidine,
2-chloro-6-methyl-4-(3,4-dichlorobenzylamino)-thieno-[2,3-d]-pyrimidine;
with 2,4-dichloro-5-methyl-thieno-[2,3-d]-pyrimidine,
2-chloro-5-methyl-4-(3,4-dichlorobenzylamino)-thieno-[2,3-d]-pyrimidine;
with 2,4-dichloro-5,6,7,8-tetrahydro-[1]-benzothieno-[2,3-d]-pyrimidine,
2-chloro-5,6,7,8-tetrahydro-4-(3,4-dichlorobenzylamino)-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-(3,4-dichlorobenzylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3,4-dichlorobenzylamino)-[1]-benzothieno-[2,3-d]-pyrimidine;
with 2,4-dichloro-6-ethyl-thieno-[2,3-d]-pyrimidine,
2-chloro-6-ethyl-4-(3,4-dichlorobenzylamino)-thieno-[2,3-d]-pyrimidine;
with 2,4,6-trichloro-thieno-[2,3-d]-pyrimidine, 2,6-dichloro-4-(3,4-dichlorobenzylamino)-thieno-[2,3-d]-pyrimidine;
with 2,4,5-trichloro-6-methyl-thieno-[2,3-d]-pyrimidine,
2,5-dichloro-6-methyl-4-(3,4-dichlorobenzylamino)-thieno-[2,3-d]-pyrimidine;
with 2,4-dichloro-6-nitro-thieno-[2,3-d]-pyrimidine,
2-chloro-6-nitro-4-(3,4-dichlorobenzylamino)-thieno-[2,3-d]-pyrimidine;
with 2,4-dichloro-5,6-dimethyl-thieno-[2,3-d]-pyrimidine,
2-chloro-5,6-dimethyl-4-(3,4-dichlorobenzylamino)-thieno-[2,3-d]-pyrimidine;
with 2,4-dichloro-6-trifluoromethyl-thieno-[2,3-d]-pyrimidine,
2-chloro-6-trifluoromethyl-4-(3,4-dichlorobenzylamino)-thieno-[2,3-d]-pyrimidine,
are obtained.

Analogously, by reaction of 3-nitrobenzylamine
with 2,4-dichloro-6-methyl-thieno-[2,3-d]-pyrimidine,
2-chloro-6-methyl-4-(3-nitrobenzylamino)-thieno-[2,3-d]-pyrimidine;
with 2,4-dichloro-5-methyl-thieno-[2,3-d]-pyrimidine,
2-chloro-5-methyl-4-(3-nitrobenzylamino)-thieno-[2,3-d]-pyrimidine;
with 2,4-dichloro-5,6,7,8-tetrahydro-[1]-benzothieno-[2,3-d]-pyrimidine,
2-chloro-5,6,7,8-tetrahydro-4-(3-nitrobenzylamino)-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-(3-nitrobenzyl-amino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3-nitrobenzyl-amino)-[1]-benzothieno-[2,3-d]-pyrimidine;
with 2,4-dichloro-6-ethyl-thieno-[2,3-d]-pyrimidine,
2-chloro-6-ethyl-4-(3-nitrobenzylamino)-thieno-[2,3-d]-pyrimidine;
with 2,4,6-trichloro-thieno-[2,3-d]-pyrimidine,
2,6-dichloro-4-(3-nitrobenzylamino)-thieno-[2,3-d]-pyrimidine;
with 2,4,5-trichloro-6-methyl-thieno-[2,3-d]-pyrimidine,
2,5-dichloro-6-methyl-4-(3-nitrobenzylamino)-thieno-[2,3-d]-pyrimidine;
with 2,4-dichloro-6-nitro-thieno-[2,3-d]-pyrimidine,
2-chloro-6-nitro-4-(3-nitrobenzylamino)-thieno-[2,3-d]-pyrimidine;
with 2,4-dichloro-5,6-dimethyl-thieno-[2,3-d]-pyrimidine,
2-chloro-5,6-dimethyl-4-(3-nitrobenzylamino)-thieno-[2,3-d]-pyrimidine;
with 2,4-dichloro-6-trifluoromethyl-thieno-[2,3-d]-pyrimidine,
2-chloro-6-trifluoromethyl-4-(3-nitrobenzylamino)-thieno-[2,3-d]-pyrimidine,
are obtained.

Analogously, by reaction of 3,4-methylenedioxyphenthylamine
with 2,4-dichloro-6-methyl-thieno-[2,3-d]-pyrimidine,
2-chloro-6-methyl-4-(3,4-methylenedioxyphenethylamino)-thieno-[2,3-d]-pyrimidine;
with 2,4-dichloro-5-methyl-thieno-[2,3-d]-pyrimidine,
2-chloro-5-methyl-4-(3,4-methylenedioxyphenethylamino)-thieno-[2,3-d]-pyrimidine;
with 2,4-dichloro-5,6,7,8-tetrahydro-[1]-benzothieno-[2,3-d]-pyrimidine,
2-chloro-5,6,7,8-tetrahydro-4-(3,4-methylenedioxyphenethylamino)-[1]-benzothieno-[2,3-d]-pyrimidine;
with 2,4-dichloro-5,6-cyclopenteno-(1)-benzothieno-[2,3-d]-pyrimidine,
2-chloro-5,6-cyclopenteno-4-(3,4-methylenedioxyphenethylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3,4-methylenedioxyphenethylamino)-[1]-benzothieno-[2,3-d]-pyrimidine;
with 2,4-dichloro-6-ethyl-thieno-[2,3-d]-pyrimidine,
2-chloro-6-ethyl-4-(3,4-methylenedioxyphenethylamino)-thieno-[2,3-d]-pyrimidine;
with 2,4,6-trichloro-thieno-[2,3-d]-pyrimidine,
2,6-dichloro-4-(3,4-methylenedioxyphenethylamino)-thieno-[2,3-d]-pyrimidine;
with 2,4,5-trichloro-6-methyl-thieno-[2,3-d]-pyrimidine,
2,5-dichloro-6-methyl-4-(3,4-methylenedioxyphenethylamino)-thieno-[2,3-d]-pyrimidine;
with 2,4-dichloro-6-nitro-thieno-[2,3-d]-pyrimidine,
2-chloro-6-nitro-4-(3,4-methylenedioxyphenethylamino)-thieno-[2,3-d]-pyrimidine;
with 2,4-dichloro-5,6-dimethyl-thieno-[2,3-d]-pyrimidine,
2-chloro-5,6-dimethyl-4-(3,4-methylenedioxyphenethylamino)-thieno-[2,3-d]-pyrimidine;
with 2,4-dichloro-6-trifluoromethyl-thieno-[2,3-d]-pyrimidine,
2-chloro-6-trifluoromethyl-4-(3,4-methylenedioxyphenethylamino)-thieno-[2,3-d]-pyrimidine,
are obtained.

Analogously, by reaction of 3,4-ethylenedioxybenzylamine
with 2,4-dichloro-6-methyl-thieno-[2,3-d]-pyrimidine,
2-chloro-6-methyl-4-(3,4-ethylenedioxybenzylamino)-thieno-[2,3-d]-pyrimidine;
with 2,4-dichloro-5-methyl-thieno-[2,3-d]-pyrimidine,
2-chloro-5-methyl-4-(3,4-ethylenedioxybenzylamino)-thieno-[2,3-d]-pyrimidine;
with 2,4-dichloro-5,6,7,8-tetrahydro-[1-benzothieno-[2,3-d]-pyrimidine,
2-chloro-5,6,7,8-tetrahydro-4-(3,4-ethylenedioxybenzylamino)-[1]-benzothieno-[2,3-d]-pyrimidine;
with 2,4-dichloro-5,6-cyclopenteno-[1]-benzothieno-[2,3-d]-pyrimidine,
2-chloro-5,6-cyclopenteno-4-(3,4-ethylenedioxybenzylamino)-[1]-benzothieno-[2,3-d]-pyrimidine;
with 2,4-dichloro-5,6-cyclohepteno-[1]-benzothieno-[2,3-d]-pyrimidine,
2-chloro-5,6-cyclohepteno-4-(3,4-ethylenedioxybenzylamino)-[1]-benzothieno-[2,3-d]-pyrimidine;
with 2,4-dichloro-6-ethyl-thieno-[2,3-d]-pyrimidine,
2-chloro-6-ethyl-4-(3,4-ethylenedioxybenzylamino)-thieno-[2,3-d]-pyrimidine;
with 2,4,6-trichloro-thieno-[2,3-d]-pyrimidine,
2,6-dichloro-4-(3,4-ethylenedioxybenzylamino)-thieno-[2,3-d]-pyrimidine;
with 2,4,5-trichloro-6-methyl-thieno-[2,3-d]-pyrimidine,
2,5-dichloro-6-methyl-4-(3,4-ethylenedioxybenzylamino)-thieno-[2,3-d]-pyrimidine;
with 2,4-dichloro-6-nitro-thieno-[2,3-d]-pyrimidine,
2-chloro-6-nitro-4-(3,4-ethylenedioxybenzylamino)-thieno-[2,3-d]-pyrimidine;

with 2,4-dichloro-5,6-dimethyl-thieno-[2,3-d]-pyrimidine,
2-chloro-5,6-dimethyl-4-(3,4-ethylenedioxybenzylamino)-thieno-[2,3-d]-pyrimidine;
with 2,4-dichloro-6-trifluoromethyl-thieno-[2,3-d]-pyrimidine,
2-chloro-6-trifluoromethyl-4-(3,4-ethylenedioxybenzylamino)-thieno-[2,3-d]-pyrimidine,
are obtained.

EXAMPLE 2

1.67 g of 2-chloro-6-methyl-4-(3,4-methylenedioxybenzylamino)-thieno-[2,3-d]-pyrimidine and 3 g of ethyl piperidine-4-carboxylate are heated at 130° for 3 hours. After cooling, the residue is dissolved in methylene chloride and the solution is worked up in the customary manner. 0.5 g of ethyl 1-[6-methyl-4-(3,4-methylenedioxybenzylamino)-thieno-[2,3-d]-pyrimidine-2-yl]-piperidine-4-carboxylate is obtained.

Analogously, the following compounds are obtained by reaction of ethyl piperidine-4-carboxylate with the 2-chloro-thieno-[2,3-d]-pyrimidine derivatives obtained under Example 1, which are substituted by arylalkylamino in the 4-position, ethyl 1-[5-methyl-4-(3,4-methylenedioxybenzylamino)-thieno-[2,3-d]-pyrimidin-2-yl]-piperidine-4-carboxylate;

ethyl 1-[5,6,7,8-tetrahydro-4-(3,4-methylenedioxybenzylamino)-[1]-benzothieno-[2,3-d]-pyrimidin-2-yl]-piperidine-4-carboxylate;

ethyl 1-[5,6-cyclopenteno-4-(3,4-methylenedioxybenzylamino)-[1]-benzothieno-[2,3-d]-pyrimidin-2-yl]-piperidine-4-carboxylate;

ethyl 1-[5,6-cyclohepteno-4-(3,4-methylenedioxybenzylamino)-[1]-benzothieno-[2,3-d]-pyrimidin-2-yl]]-piperidine-4-carboxylate;

ethyl 1-[6-ethyl-4-(3,4-methylenedioxybenzylamino)-thieno-[2,3-d]-pyrimidin-2-yl]-piperidine-4-carboxylate;

ethyl 1-[6-chloro-4-(3,4-methylenedioxybenzylamino)-thieno-[2,3-d]-pyrimidin-2-yl]-piperidine-4-carboxylate;

ethyl 1-[5-chloro-6-methyl-4-(3,4-methylenedioxybenzylamino)-thieno-[2,3-d]-pyrimidin-2-yl]-piperidine-4-carboxylate;

ethyl 1-[6-nitro-4-(3,4-methylenedioxybenzylamino)-thieno-[2,3-d]-pyrimidin-2-yl]-piperidine-4-carboxylate;

ethyl 1-[5,6-dimethyl-4-(3,4-methylenedioxybenzylamino)-thieno-[2,3-d]-pyrimidin-2-yl]-piperidine-4-carboxylate;

ethyl 1-[6-trifluoromethyl-4-(3,4-methylenedioxybenzylamino)-thieno-[2,3-d]-pyrimidin-2-yl]-piperidine-4-carboxylate;

ethyl 1-[6-methyl-4-(3-chloro-4-methoxybenzylamino)-thieno-[2,3-d]-pyrimidin-2-yl]-piperidine-4-carboxylate;

ethyl 1-[5-methyl-4-(3-chloro-4-methoxybenzylamino)-thieno-[2,3-d]-pyrimidin-2-yl]-piperidine-4-carboxylate;

ethyl 1-[5,6,7,8-tetrahydro-4-(3-chloro-4-methoxybenzylamino)-[1]-benzothieno-[2,3-d]-pyrimidin-2-yl]-piperidine-4-carboxylate;

ethyl 1-[5,6-cyclopenteno-4-(3-chloro-4-methoxybenzylamino)-[1]-benzothieno-[2,3-d]-pyrimidin-2-yl]-piperidine-4-carboxylate;

ethyl 1-[5,6-cyclohepteno-4-(3-chloro-4-methoxybenzylamino)-[1]-benzothieno-[2,3-d]-pyrimidin-2-yl]-piperidine-4-carboxylate;

ethyl 1-[6-ethyl-4-(3-chloro-4-methoxybenzylamino)-thieno-[2,3-d]-pyrimidin-2-yl]-piperidine-4-carboxylate;

ethyl 1-[6-chloro-4-(3-chloro-4-methoxybenzylamino)-thieno-[2,3-d]-pyrimidin-2-yl]-piperidine-4-carboxylate;

ethyl 1-[5-chloro-6-methyl-4-(3-chloro-4-methoxybenzylamino)-thieno-[2,3-d]-pyrimidin-2-yl]-piperidine-4-carboxylate;

ethyl 1-[6-nitro-4-(3-chloro-4-methoxybenzylamino)-thieno-[2,3-d]-pyrimidin-2-yl]-piperidine-4-carboxylate;

ethyl 1-[5,6-dimethyl-4-(3-chloro-4-methoxybenzylamino)-thieno-[2,3-d]-pyrimidin-2-yl]-piperidine-4-carboxylate;

ethyl 1-[6-trifluoromethyl-4-(3-chloro-4-methoxybenzylamino)-thieno-[2,3-d]-pyrimidin-2-yl]-piperidine-4-carboxylate;

ethyl 1-[6-methyl-4-(3,4-dimethoxybenzylamino)-thieno-[2,3-d]-pyrimidin-2-yl]-piperidine-4-carboxylate;

ethyl 1-[5-methyl-4-(3,4-dimethoxybenzylamino)-thieno-[2,3-d]-pyrimidin-2-yl]-piperidine-4-carboxylate;

ethyl 1-[5,6,7,8-tetrahydro-4-(3,4-dimethoxybenzylamino)-[1]-benzothieno-[2,3-d]-pyrimidin-2-yl]-piperidine-4-carboxylate;

ethyl 1-[5,6-cyclopenteno-4-(3,4-dimethoxybenzylamino)-[1]-benzothieno-[2,3-d]-pyrimidin-2-yl]-piperidine-4-carboxylate;

ethyl 1-[5,6-cyclohepteno-4-(3,4-dimethoxybenzylamino)-[1]-benzothieno-[2,3-d]-pyrimidin-2-yl]-piperidine-4-carboxylate;

ethyl 1-[6-ethyl-4-(3,4-dimethoxybenzylamino)-thieno-[2,3-d]-pyrimidin-2-yl]-piperidine-4-carboxylate;

ethyl 1-[6-chloro-4-(3,4-dimethoxybenzylamino)-thieno-[2,3-d]-pyrimidin-2-yl]-piperidine-4-carboxylate;

ethyl 1-[5-chloro-6-methyl-4-(3,4-dimethoxybenzylamino)-thieno-[2,3-d]-pyrimidin-2-yl]-piperidine-4-carboxylate;

ethyl 1-[6-nitro-4-(3,4-dimethoxybenzylamino)-thieno-[2,3-d]-pyrimidin-2-yl]-piperidine-4-carboxylate;

ethyl 1-[5,6-dimethyl-4-(3,4-dimethoxybenzylamino)-thieno-[2,3-d]-pyrimidin-2-yl]-piperidine-4-carboxylate;

ethyl 1-[6-trifluoromethyl-4-(3,4-dimethoxybenzylamino)-thieno-[2,3-d]-pyrimidin-2-yl]-piperidine-4-carboxylate;

ethyl 1-[6-methyl-4-(3,4-dimethoxybenzylamino)-thieno-[2,3-d]-pyrimidin-2-yl]-piperidine-4-carboxylate;

ethyl 1-(6-methyl-4-benzylamino-thieno-[2,3-d]-pyrimidin-2-yl)-piperidine-4-carboxylate;

ethyl 1-(5-methyl-4-benzylamino-thieno-[2,3-d]-pyrimidin-2-yl)-piperidine-4-carboxylate;

ethyl 1-(5,6,7,8-tetrahydro-4-benzylamino-[1]-benzothieno-[2,3-d]-pyrimidin-2-yl)-piperidine-4-carboxylate;

ethyl 1-(5,6-cyclopenteno-4-benzylamino-[1]-benzothieno-[2,3-d]-pyrimidin-2-yl)-piperidine-4-carboxylate;

ethyl 1-(5,6-cyclohepteno-4-benzylamino-[1]-benzothieno-[2,3-d]-pyrimidin-2-yl)-piperidine-4-carboxylate;

ethyl 1-(6-ethyl-4-benzylamino-thieno-[2,3-d]-pyrimidin-2-yl)-piperidine-4-carboxylate;

ethyl 1-(6-chloro-4-benzylamino-thieno-[2,3-d]-pyrimidin-2-yl)-piperidine-4-carboxylate;

ethyl 1-(5-chloro-6-methyl-4-benzylamino-thieno-[2,3-d]-pyrimidin-2-yl)-piperidine-4-carboxylate;

ethyl 1-(6-nitro-4-benzylamino-thieno-[2,3-d]-pyrimidin-2-yl)-piperidine-4-carboxylate;

ethyl 1-(5,6-dimethyl-4-benzylamino-thieno-[2,3-d]-pyrimidin-2-yl)-piperidine-4-carboxylate;

ethyl 1-(6-trifluoromethyl-4-benzylamino-thieno-[2,3-d]-pyrimidin-2-yl)-piperidine-4-carboxylate;

ethyl 1-[6-methyl-4-(4-fluorobenzylamino)-thieno-[2,3-d]-pyrimidin-2-yl]-piperidine-4-carboxylate;

ethyl 1-[5-methyl-4-(4-fluorobenzylamino)-thieno-[2,3-d]-pyrimidin-2-yl]-piperidine-4-carboxylate;

ethyl 1-[5,6,7,8-tetrahydro-4-(4-fluorobenzylamino)-[1]-benzothieno-[2,3-d]-pyrimidin-2-yl]-piperidine-4-carboxylate;

ethyl 1-[5,6-cyclopenteno-4-(4-fluorobenzylamino)-[1]-benzothieno-[2,3-d]-pyrimidin-2-yl]-piperidine-4-carboxylate;

ethyl 1-[5,6-cyclohepteno-4-(4-fluorobenzylamino)-[1]-benzothieno-[2,3-d]-pyrimidin-2-yl]-piperidine-4-carboxylate;

ethyl 1-[6-ethyl-4-(4-fluorobenzylamino)-thieno-[2,3-d]-pyrimidin-2-yl]-piperidine-4-carboxylate;
ethyl 1-[6-chloro-4-(4-fluorobenzylamino)-thieno-[2,3-d]-pyrimidin-2-yl]-piperidine-4-carboxylate;
ethyl 1-[5-chloro-6-methyl-4-(4-fluorobenzylamino)-thieno-[2,3-d]-pyrimidin-2-yl]-piperidine-4-carboxylate;
ethyl 1-[6-nitro-4-(4-fluorobenzylamino)-thieno-[2,3-d]-pyrimidin-2-yl]-piperidine-4-carboxylate;
ethyl 1-[5,6-dimethyl-4-(4-fluorobenzylamino)-thieno-[2,3-d]-pyrimidin-2-yl]-piperidine-4-carboxylate;
ethyl 1-[6-trifluoromethyl-4-(4-fluorobenzylamino)-thieno-[2,3-d]-pyrimidin-2-yl]-piperidine-4-carboxylate;
ethyl 1-[6-methyl-4-(3,4-dichlorobenzylamino)-thieno-[2,3-d]-pyrimidin-2-yl]-piperidine-4-carboxylate;
ethyl 1-[5-methyl-4-(3,4-dichlorobenzylamino)-thieno-[2,3-d]-pyrimidin-2-yl]-piperidine-4-carboxylate;
ethyl 1-[5,6,7,8-tetrahydro-4-(3,4-dichlorobenzylamino)-[1]-benzothieno-[2,3-d]-pyrimidin-2-yl]-piperidine-4-carboxylate;
ethyl 1-[5,6-cyclopenteno-4-(3,4-dichlorobenzylamino)-[1]-benzothieno-[2,3-d]-pyrimidin-2-yl]-piperidine-4-carboxylate;
ethyl 1-[5,6-cyclohepteno-4-(3,4-dichlorobenzylamino)-[1]-benzothieno-[2,3-d]-pyrimidin-2-yl]-piperidine-4-carboxylate;
ethyl 1-[6-ethyl-4-(3,4-dichlorobenzylamino)-thieno-[2,3-d]-pyrimidin-2-yl]-piperidine-4-carboxylate;
ethyl 1-[6-chloro-4-(3,4-dichlorobenzylamino)-thieno-[2,3-d]-pyrimidin-2-yl]-piperidine-4-carboxylate;
ethyl 1-[5-chloro-6-methyl-4-(3,4-dichlorobenzylamino)-thieno-[2,3-d]-pyrimidin-2-yl]-piperidine-4-carboxylate;
ethyl 1-[6-nitro-4-(3,4-dichlorobenzylamino)-thieno-[2,3-d]-pyrimidin-2-yl]-piperidine-4-carboxylate;
ethyl 1-[5,6-dimethyl-4-(3,4-dichlorobenzylamino)-thieno-[2,3-d]-pyrimidin-2-yl]-piperidine-4-carboxylate;
ethyl 1-[6-trifluoromethyl-4-(3,4-dichlorobenzylamino)-thieno-[2,3-d]-pyrimidin-2-yl]-piperidine-4-carboxylate;
ethyl 1-[6-methyl-4-(3-nitrobenzylamino)-thieno-[2,3-d]-pyrimidin-2-yl]-piperidine-4-carboxylate;
ethyl 1-[5-methyl-4-(3-nitrobenzylamino)-thieno-[2,3-d]-pyrimidin-2-yl]-piperidine-4-carboxylate;
ethyl 1-[5,6,7,8-tetrahydro-4-(3-nitrobenzylamino)-[1]-benzothieno-[2,3-d]-pyrimidin-2-yl]-piperidine-4-carboxylate;
ethyl 1-[5,6-cyclopenteno-4-(3-nitrobenzylamino)-[1]-benzothieno-[2,3-d]-pyrimidin-2-yl]-piperidine-4-carboxylate;
ethyl 1-[5,6-cyclohepteno-4-(3-nitrobenzylamino)-[1]-benzothieno-[2,3-d]-pyrimidin-2-yl]-piperidine-4-carboxylate;
ethyl 1-[6-ethyl-4-(3-nitrobenzylamino)-thieno-[2,3-d]-pyrimidin-2-yl]-piperidine-4-carboxylate;
ethyl 1-[6-chloro-4-(3-nitrobenzylamino)-thieno-[2,3-d]-pyrimidin-2-yl]-piperidine-4-carboxylate;
ethyl 1-[5-chloro-6-methyl-4-(3-nitrobenzylamino)-thieno-[2,3-d]-pyrimidin-2-yl]-piperidine-4-carboxylate;
ethyl 1-[6-nitro-4-(3-nitrobenzylamino)-thieno-[2,3-d]-pyrimidin-2-yl]-piperidine-4-carboxylate;
ethyl 1-[5,6-dimethyl-4-(3-nitrobenzylamino)-thieno-[2,3-d]-pyrimidin-2-yl]-piperidine-4-carboxylate;
ethyl 1-[6-trifluoromethyl-4-(3-nitrobenzylamino)-thieno-[2,3-d]-pyrimidin-2-yl]-piperidine-4-carboxylate;
ethyl 1-[6-methyl-4-(3,4-methylenedioxyphenethylamino)-thieno-[2,3-d]-pyrimidin-2-yl]-piperidine-4-carboxylate;
ethyl 1-[5-methyl-4-(3,4-methylenedioxyphenethylamino)-thieno-[2,3-d]-pyrimidin-2-yl]-piperidine-4-carboxylate;
ethyl 1-[5,6,7,8-tetrahydro-4-(3,4-methylenedioxyphenethylamino)-[1]-benzothieno-[2,3-d]-pyrimidin-2-yl]-piperidine-4-carboxylate;
ethyl 1-[5,6-cyclopenteno-4-(3,4-methylenedioxyphenethylamino)-[1]-benzothieno-[2,3-d]-pyrimidin-2-yl]-piperidine-4-carboxylate;
ethyl 1-[5,6-cyclohepteno-4-(3,4-methylenedioxyphenethylamino)-[1]-benzothieno-[2,3-d]-pyrimidin-2-yl]-piperidine-4-carboxylate;
ethyl 1-[6-ethyl-4-(3,4-methylenedioxyphenethylamino)-thieno-[2,3-d]-pyrimidin-2-yl]-piperidine-4-carboxylate;
ethyl 1-[6-chloro-4-(3,4-methylenedioxyphenethylamino)-thieno-[2,3-d]-pyrimidin-2-yl]-piperidine-4-carboxylate;
ethyl 1-[5-chloro-6-methyl-4-(3,4-methylenedioxyphenethylamino)-thieno-[2,3-d]-pyrimidin-2-yl]-piperidine-4-carboxylate;
ethyl 1-[6-nitro-4-(3,4-methylenedioxyphenethylamino)-thieno-[2,3-d]-pyrimidin-2-yl]-piperidine-4-carboxylate;
ethyl 1-[5,6-dimethyl-4-(3,4-methylenedioxyphenethylamino)-thieno-[2,3-d]-pyrimidin-2-yl]-piperidine-4-carboxylate;
ethyl 1-[6-trifluoromethyl-4-(3,4-methylenedioxyphenethylamino)-thieno-[2,3-d]-pyrimidin-2-yl]-piperidine-4-carboxylate;
ethyl 1-[6-methyl-4-(3,4-ethylenedioxybenzylamino)-thieno-[2,3-d]-pyrimidin-2-yl]-piperidine-4-carboxylate;
ethyl 1-[5-methyl-4-(3,4-ethylenedioxybenzylamino)-thieno-[2,3-d]-pyrimidin-2-yl]-piperidine-4-carboxylate;
ethyl 1-[5,6,7,8-tetrahydro-4-(3,4-ethylenedioxybenzylamino)-[1]-benzothieno-[2,3-d]-pyrimidin-2-yl]-piperidine-4-carboxylate;
ethyl 1-[5,6-cyclopenteno-4-(3,4-ethylenedioxybenzylamino)-[1]-benzothieno-[2,3-d]-pyrimidin-2-yl]-piperidine-4-carboxylate;
ethyl 1-[5,6-cyclohepteno-4-(3,4-ethylenedioxybenzylamino)-[1]-benzothieno-[2,3-d]-pyrimidin-2-yl]-piperidine-4-carboxylate;
ethyl 1-[6-ethyl-4-(3,4-ethylenedioxybenzylamino)-thieno-[2,3-d]-pyrimidin-2-yl]-piperidine-4-carboxylate;
ethyl 1-[6-chloro-4-(3,4-ethylenedioxybenzylamino)-thieno-[2,3-d]-pyrimidin-2-yl]-piperidine-4-carboxylate;
ethyl 1-[5-chloro-6-methyl-4-(3,4-ethylenedioxybenzylamino)-thieno-[2,3-d]-pyrimidin-2-yl]-piperidine-4-carboxylate;
ethyl 1-[6-nitro-4-(3,4-ethylenedioxybenzylamino)-thieno-[2,3-d]-pyrimidin-2-yl]-piperidine-4-carboxylate;
ethyl 1-[5,6-dimethyl-4-(3,4-ethylenedioxybenzylamino)-thieno-[2,3-d]-pyrimidin-2-yl]-piperidine-4-carboxylate;
ethyl 1-[6-trifluoromethyl-4-(3,4-ethylenedioxybenzylamino)-thieno-[2,3-d]-pyrimidin-2-yl]-piperidine-4-carboxylate.

EXAMPLE 3

0.5 g of ethyl 1-[6-methyl-4-(3,4-methylenedioxybenzylamino)-thieno-[2,3-d]-pyrimidin-2-yl]-piperidine-4-carboxylate is dissolved in 70 ml of methanol and, after addition of 30 ml of 2N NaOH, the mixture is stirred at 500 for 4 hours. After the solvent has been removed and the residue has been washed with cold water, 1.5 g of the sodium salt of 1-[6-methyl-4-(3,4-methylenedioxybenzylamino)-thieno-[2,3-d]-pyrimidin-2-yl]-piperidine-4-carboxylic acid are obtained, m.p. 272°.

Analogously, the following carboxylic acids are obtained from the esters listed under Example 2:
1-[5-methyl-4-(3,4-methylenedioxybenzylamino)-thieno-[2,3-d]-pyrimidin-2-yl]-piperidine-4-carboxylic acid;
1-[5,6,7,8-tetrahydro-4-(3,4-methylenedioxybenzylamino)-[1]-benzothieno-[2,3-d]-pyrimidin-2-yl]-piperidine-4-carboxylic acid, monohydrate, amorphous (decomposition);

1-[5,6-cyclopenteno-4-(3,4-methylenedioxybenzylamino)-[1]-benzothieno-[2,3-d]-pyrimidin-2-yl]-piperidine-4-carboxylic acid, m.p. >250°;

1-[5,6-cyclohepteno-4-(3,4-methylenedioxybenzylamino)-[1]-benzothieno-[2,3-d]-pyrimidin-2-yl]-piperidine-4-carboxylic acid, m.p. 217°;

1-[6-ethyl-4-(3,4-methylenedioxybenzylamino)-thieno-[2,3-d]-pyrimidin-2-yl]-piperidine-4-carboxylic acid;

1-[6-chloro-4-(3,4-methylenedioxybenzylamino)-thieno-[2,3-d]-pyrimidin-2-yl]-piperidine-4-carboxylic acid;

1-[5-chloro-6-methyl-4-(3,4-methylenedioxybenzylamino)-thieno-[2,3-d]-pyrimidin-2-yl]-piperidine-4-carboxylic acid, amorphous (decomposition);

1-[6-nitro-4-(3,4-methylenedioxybenzylamino)-thieno-[2,3-d]-pyrimidin-2-yl]-piperidine-4-carboxylic acid amorphous (decomposition);

1-[5,6-dimethyl-4-(3,4-methylenedioxybenzyl-amino)-thieno-[2,3-d]-pyrimidin-2-yl]-piperidine-4-carboxylic acid;

1-[6-trifluoromethyl-4-(3,4-methylenedioxybenzylamino)-thieno-[2,3-d]-pyrimidin-2-yl]-piperidine-4-carboxylic acid;

1-[6-methyl-4-(3-chloro-4-methoxybenzylamino)-thieno-[2,3-d]-pyrimidin-2-yl]-piperidine-4-carboxylic acid;

1-[5-methyl-4-(3-chloro-4-methoxybenzylamino)-thieno-[2,3-d]-pyrimidin-2-yl]-piperidine-4-carboxylic acid;

1-[5,6,7,8-tetrahydro-4-(3-chloro-4-methoxybenzylamino)-[1]-benzothieno-[2,3-d]-pyrimidin-2-yl]-piperidine-4-carboxylic acid, sodium salt, m.p. 213°;

1-[5,6-cyclopenteno-4-(3-chloro-4-methoxybenzyl-amino)-[1]-benzothieno-[2,3-d]-pyrimidin-2-yl]-piperidine-4-carboxylic acid, sodium salt, m.p. >250°; potassium salt, m.p. >250°;

1-[5,6-cyclohepteno-4-(3-chloro-4-methoxybenzyl-amino)-[1]-benzothieno-[2,3-d]-pyrimidin-2-yl]-piperidine-4-carboxylic acid;

1-[6-ethyl-4-(3-chloro-4-methoxybenzylamino)-thieno-[2,3-d]-pyrimidin-2-yl]-piperidine-4-carboxylic acid;

1-[6-chloro-4-(3-chloro-4-methoxybenzylamino)-thieno-[2,3-d]-pyrimidin-2-yl]-piperidine-4-carboxylic acid;

1-[5-chloro-6-methyl-4-(3-chloro-4-methoxybenzylamino)-thieno-[2,3-d]-pyrimidin-2-yl]-piperidine-4-carboxylic acid, sodium salt, m.p. >250°;

1-[6-nitro-4-(3-chloro-4-methoxybenzylamino)-thieno-[2,3-d]-pyrimidin-2-yl]-piperidine-4-carboxylic acid;

1-[5,6-dimethyl-4-(3-chloro-4-methoxybenzyl-amino)-thieno-[2,3-d]-pyrimidin-2-yl]-piperidine-4-carboxylic acid, sodium salt, amorphous;

1-[6-trifluoromethyl-4-(3-chloro-4-methoxybenzylamino)-thieno-[2,3-d]-pyrimidin-2-yl]-piperidine-4-carboxylic acid;

1-[6-methyl-4-(3,4-dimethoxybenzylamino)-thieno-[2,3-d]-pyrimidin-2-yl]-piperidine-4-carboxylic acid;

1-[5-methyl-4-(3,4-dimethoxybenzylamino)-thieno-[2,3-d]-pyrimidin-2-yl]-piperidine-4-carboxylic acid;

1-[5,6,7,8-tetrahydro-4-(3,4-dimethoxybenzylamino)-[1]-benzothieno-[2,3-d]-pyrimidin-2-yl]-piperidine-4-carboxylic acid;

1-[5,6-cyclopenteno-4-(3,4-dimethoxybenzylamino)-[1]-benzothieno-[2,3-d]-pyrimidin-2-yl]-piperidine-4-carboxylic acid;

1-[5,6-cyclohepteno-4-(3,4-dimethoxybenzylamino)-[1]-benzothieno-[2,3-d]-pyrimidin-2-yl]-piperidine-4-carboxylic acid;

1-[6-ethyl-4-(3,4-dimethoxybenzylamino)-thieno-[2,3-d]-pyrimidin-2-yl]-piperidine-4-carboxylic acid;

1-[6-chloro-4-(3,4-dimethoxybenzylamino)-thieno-[2,3-d]-pyrimidin-2-yl]-piperidine-4-carboxylic acid;

1-[5-chloro-6-methyl-4-(3,4-dimethoxybenzylamino)-thieno-[2,3-d]-pyrimidin-2-yl]-piperidine-4-carboxylic acid;

1-[6-nitro-4-(3,4-dimethoxybenzylamino)-thieno-[2,3-d]-pyrimidin-2-yl]-piperidine-4-carboxylic acid;

1-[5,6-dimethyl-4-(3,4-dimethoxybenzylamino)-thieno-[2,3-d]-pyrimidin-2-yl]-piperidine-4-carboxylic acid;

1-[6-trifluoromethyl-4-(3,4-dimethoxybenzylamino)-thieno-[2,3-d]-pyrimidin-2-yl]-piperidine-4-carboxylic acid;

1-[6-methyl-4-(3,4-dimethoxybenzylamino)-thieno-[2,3-d]-pyrimidin-2-yl]-piperidine-4-carboxylic acid, m.p. 203°;

1-(6-methyl-4-benzylamino-thieno-[2,3-d]-pyrimidin-2-yl)-piperidine-4-carboxylic acid;

1-(5-methyl-4-benzylamino-thieno-[2,3-d]-pyrimidin-2-yl)-piperidine-4-carboxylic acid;

1-(5,6,7,8-tetrahydro-4-benzylamino-[1]-benzothieno-[2,3-d]-pyrimidin-2-yl)-piperidine-4-carboxylic acid;

1-(5,6-cyclopenteno-4-benzylamino-[1]-benzothieno-[2,3-d]-pyrimidin-2-yl)-piperidine-4-carboxylic acid;

1-(5,6-cyclohepteno-4-benzylamino-[1]-benzothieno-[2,3-d]-pyrimidin-2-yl)-piperidine-4-carboxylic acid, m.p. 257°;

1-(6-ethyl-4-benzylamino-thieno-[2,3-d]-pyrimidin-2-yl)-piperidine-4-carboxylic acid, sodium salt, amorphous;

1-(6-chloro-4-benzylamino-thieno-[2,3-d]-pyrimidin-2-yl)-piperidine-4-carboxylic acid;

1-(5-chloro-6-methyl-4-benzylamino-thieno-[2,3-d]-pyrimidin-2-yl)-piperidine-4-carboxylic acid;

1-(6-nitro-4-benzylamino-thieno-[2,3-d]-pyrimidin-2-yl)-piperidine-4-carboxylic acid;

1-(5,6-dimethyl-4-benzylamino-thieno-[2,3-d]-pyrimidin-2-yl)-piperidine-4-carboxylic acid;

1-(6-trifluoromethyl-4-benzylamino-thieno-[2,3-d]-pyrimidin-2-yl)-piperidine-4-carboxylic acid;

1-[6-methyl-4-(4-fluorobenzylamino)-thieno-[2,3-d]-pyrimidin-2-yl]-piperidine-4-carboxylic acid;

1-[5-methyl-4-(4-fluorobenzylamino)-thieno-[2,3-d]-pyrimidin-2-yl]-piperidine-4-carboxylic acid;

1-[5,6,7,8-tetrahydro-4-(4-fluorobenzylamino)-[1]-benzothieno-[2,3-d]-pyrimidin-2-yl]-piperidine-4-carboxylic acid, sodium salt, m.p. 279°;

1-[5,6-cyclopenteno-4-(4-fluorobenzylamino)-[1]-benzothieno-[2,3-d]-pyrimidin-2-yl]-piperidine-4-carboxylic acid;

1-[5,6-cyclohepteno-4-(4-fluorobenzylamino)-[1]-benzothieno-[2,3-d]-pyrimidin-2-yl]-piperidine-4-carboxylic acid;

1-[6-ethyl-4-(4-fluorobenzylamino)-thieno-[2,3-d]-pyrimidin-2-yl]-piperidine-4-carboxylic acid;

1-[6-chloro-4-(4-fluorobenzylamino)-thieno-[2,3-d]-pyrimidin-2-yl]-piperidine-4-carboxylic acid;

1-[5-chloro-6-methyl-4-(4-fluorobenzylamino)-thieno-[2,3-d]-pyrimidin-2-yl]-piperidine-4-carboxylic acid;

1-[6-nitro-4-(4-fluorobenzylamino)-thieno-[2,3-d]-pyrimidin-2-yl]-piperidine-4-carboxylic acid;

1-[5,6-dimethyl-4-(4-fluorobenzylamino)-thieno-[2,3-d]-pyrimidin-2-yl]-piperidine-4-carboxylic acid;

1-[6-trifluoromethyl-4-(4-fluorobenzylamino)-thieno-[2,3-d]-pyrimidin-2-yl]-piperidine-4-carboxylic acid;

1-[6-methyl-4-(3,4-dichlorobenzylamino)-thieno-[2,3-d]-pyrimidin-2-yl]-piperidine-4-carboxylic acid;

1-[5-methyl-4-(3,4-dichlorobenzylamino)-thieno-[2,3-d]-pyrimidin-2-yl]-piperidine-4-carboxylic acid;

1-[5,6,7,8-tetrahydro-4-(3,4-dichlorobenzylamino)-[1]-benzothieno-[2,3-d]-pyrimidin-2-yl]-piperidine-4-carboxylic acid;

1-[5,6-cyclopenteno-4-(3,4-dichlorobenzylamino)-[1]-benzothieno-[2,3-d]-pyrimidin-2-yl]-piperidine-4-carboxylic acid;
1-[5,6-cycloheptena-4-(3,4-dichlorobenzylamino)-[1]-benzothieno-[2,3-d]-pyrimidin-2-yl]-piperidine-4-carboxylic acid;
1-[6-ethyl-4-(3,4-dichlorobenzylamino)-thieno-[2,3-d]-pyrimidin-2-yl]-piperidine-4-carboxylic acid;
1-[6-chloro-4-(3,4-dichlorobenzylamino)-thieno-[2,3-d]-pyrimidin-2-yl]-piperidine-4-carboxylic acid;
1-[5-chloro-6-methyl-4-(3,4-dichlorobenzylamino)-thieno-[2,3-d]-pyrimidin-2-yl]-piperidine-4-carboxylic acid;
1-[6-nitro-4-(3,4-dichlorobenzylamino)-thieno-[2,3-d]-pyrimidin-2-yl]-piperidine-4-carboxylic acid;
1-[5,6-dimethyl-4-(3,4-dichlorobenzylamino)-thieno-[2,3-d]-pyrimidin-2-yl]-piperidine-4-carboxylic acid;
1-[6-trifluoromethyl-4-(3,4-dichlorobenzylamino)-thieno-[2,3-d]-pyrimidin-2-yl]-piperidine-4-carboxylic acid;
1-[6-methyl-4-(3-nitrobenzylamino)-thieno-[2,3-d]-pyrimidin-2-yl]-piperidine-4-carboxylic acid;
1-[5-methyl-4-(3-nitrobenzylamino)-thieno-[2,3-d]-pyrimidin-2-yl]-piperidine-4-carboxylic acid;
1-[5,6,7,8-tetrahydro-4-(3-nitrobenzylamino)-[1]-benzothieno-[2,3-d]-pyrimidin-2-yl]-piperidine-4-carboxylic acid;
1-[5,6-cyclopenteno-4-(3-nitrobenzylamino)-[1]-benzothieno-[2,3-d]-pyrimidin-2-yl]-piperidine-4-carboxylic acid;
1-[5,6-cycloheptena-4-(3-nitrobenzylamino)-[1]-benzothieno-[2,3-d]-pyrimidin-2-yl]-piperidine-4-carboxylic acid;
1-[6-ethyl-4-(3-nitrobenzylamino)-thieno-[2,3-d]-pyrimidin-2-yl]-piperidine-4-carboxylic acid;
1-[6-chloro-4-(3-nitrobenzylamino)-thieno-[2,3-d]-pyrimidin-2-yl]-piperidine-4-carboxylic acid;
1-[5-chloro-6-methyl-4-(3-nitrobenzylamino)-thieno-[2,3-d]-pyrimidin-2-yl]-piperidine-4-carboxylic acid;
1-[6-nitro-4-(3-nitrobenzylamino)-thieno-[2,3-d]-pyrimidin-2-yl]-piperidine-4-carboxylic acid;
1-[5,6-dimethyl-4-(3-nitrobenzylamino)-thieno-[2,3-d]-pyrimidin-2-yl]-piperidine-4-carboxylic acid;
1-[6-trifluoromethyl-4-(3-nitrobenzylamino)-thieno-[2,3-d]-pyrimidin-2-yl]-piperidine-4-carboxylic acid;
1-[6-methyl-4-(3,4-methylenedioxyphenethylamino)-thieno-[2,3-d]-pyrimidin-2-yl]-piperidine-4-carboxylic acid;
1-[5-methyl-4-(3,4-methylenedioxyphenethylamino)-thieno-[2,3-d]-pyrimidin-2-yl]-piperidine-4-carboxylic acid;
1-[5,6,7,8-tetrahydro-4-(3,4-methylenedioxyphenethylamino)-[1]-benzothieno-[2,3-d]-pyrimidin-2-yl]-piperidine-4-carboxylic acid;
1-[5,6-cyclopenteno-4-(3,4-methylenedioxyphenethylamino)-[1]-benzothieno-[2,3-d]-pyrimidin-2-yl]-piperidine-4-carboxylic acid;
1-[5,6-cycloheptena-4-(3,4-methylenedioxyphenethylamino)-[1]-benzothieno-[2,3-d]-pyrimidin-2-yl]-piperidine-4-carboxylic acid;
1-[6-ethyl-4-(3,4-methylenedioxyphenethylamino)-thieno-[2,3-d]-pyrimidin-2-yl]-piperidine-4-carboxylic acid;
1-[6-chloro-4-(3,4-methylenedioxyphenethylamino)-thieno-[2,3-d]-pyrimidin-2-yl]-piperidine-4-carboxylic acid;
1-[5-chloro-6-methyl-4-(3,4-methylenedioxyphenethylamino)-thieno-[2,3-d]-pyrimidin-2-yl]-piperidine-4-carboxylic acid;
1-[6-nitro-4-(3,4-methylenedioxyphenethylamino)-thieno-[2,3-d]-pyrimidin-2-yl]-piperidine-4-carboxylic acid;
1-[5,6-dimethyl-4-(3,4-methylenedioxyphenethylamino)-thieno-[2,3-d]-pyrimidin-2-yl]-piperidine-4-carboxylic acid;
1-[6-trifluoromethyl-4-(3,4-methylenedioxyphenethylamino)-thieno-[2,3-d]-pyrimidin-2-yl]-piperidine-4-carboxylic acid;
1-[6-methyl-4-(3,4-ethylenedioxybenzylamino)-thieno-[2,3-d]-pyrimidin-2-yl]-piperidine-4-carboxylic acid;
1-[5-methyl-4-(3,4-ethylenedioxybenzylamino)-thieno-[2,3-d]-pyrimidin-2-yl]-piperidine-4-carboxylic acid;
1-[5,6,7,8-tetrahydro-4-(3,4-ethylenedioxybenzylamino)-[1]-benzothieno-[2,3-d]-pyrimidin-2-yl]-piperidine-4-carboxylic acid;
1-[5,6-cyclopenteno-4-(3,4-ethylenedioxybenzyl-amino)-[1]-benzothieno-[2,3-d]-pyrimidin-2-yl]-piperidine-4-carboxylic acid;
1-[5,6-cycloheptena-4-(3,4-ethylenedioxybenzyl-amino)-[1]-benzothieno-[2,3-d]-pyrimidin-2-yl]-piperidine-4-carboxylic acid;
1-[6-ethyl-4-(3,4-ethylenedioxybenzylamino)-thieno-[2,3-d]-pyrimidin-2-yl]-piperidine-4-carboxylic acid;
1-[6-chloro-4-(3,4-ethylenedioxybenzylamino)-thieno-[2,3-d]-pyrimidin-2-yl]-piperidine-4-carboxylic acid;
1-[5-chloro-6-methyl-4-(3,4-ethylenedioxybenzylamino)-thieno-[2,3-d]-pyrimidin-2-yl]-piperidine-4-carboxylic acid;
1-[6-nitro-4-(3,4-ethylenedioxybenzylamino)-thieno-[2,3-d]-pyrimidin-2-yl]-piperidine-4-carboxylic acid;
1-[5,6-dimethyl-4-(3,4-ethylenedioxybenzyl-amino)-thieno-[2,3-d]-pyrimidin-2-yl]-piperidine-4-carboxylic acid;
1-[6-trifluoromethyl-4-(3,4-ethylenedioxybenzyl-amino)-thieno-[2,3-d]-pyrimidin-2-yl]-piperidine-4-carboxylic acid.

EXAMPLE 4

5 g of 2-amino-5-methyl-3-ethoxycarbonyl-thiophene is dissolved with 2.7 g of methyl 4-cyanobenzoate in 40 ml of dioxane. Gaseous HCl is then passed through the solution for 5 hours. After customary working up, 6 g of methyl 4-(3,4-dihydro-4-oxo-6-methyl-thieno-[2,3-d]-pyrimidin-2-yl)-benzoate are obtained.

The carbonyl group is replaced by Cl to form the aromatic pyrimidine ring under standard conditions.

A mixture of 18 ml of POCl$_3$ with 6 g of methyl 4-(3,4-dihydro-4-oxo-6-methyl-thieno-[2,3-d]-pyrimidin-2-yl)-benzoate is boiled for 4 hours with the addition of 1.8 ml of N,N-dimethylaniline. Customary working up gives 5 g of methyl 4-(4-chloro-6-methyl-thieno-[2,3-d]-pyrimidin-2-yl)-benzoate.

Analogously, by reaction of methyl 4-cyanobenzoate and subsequent reaction with POCB$_3$,
from 2-amino-4-methyl-3-ethoxycarbonyl-thiophene
methyl 4-(4-chloro-5-methyl-thieno-[2,3-d]-pyrimidin-2-yl)-benzoate;
from 2-amino-4,5,6,7-tetrahydro-3-ethoxycarbonylbenzothiophene
methyl 4-(4-chloro-5,6,7,8-tetrahydro-[1]-benzothieno-[2,3-d]-pyrimidin-2-yl)-benzoate;
from 2-amino-4,5-cyclopenteno-3-ethoxycarbonylthiophene
methyl 4-(4-chloro-5,6-cyclopenteno-thieno-[2,3-d]-pyrimidin-2-yl)-benzoate;
from 2-amino-4,5-cycloheptena-3-ethoxycarbonylthiophene
methyl 4-(4-chloro-5,6-cycloheptena-thieno-[2,3-d]-pyrimidin-2-yl)-benzoate;

from 2-amino-5-ethyl-3-ethoxycarbonyl-thiophene
methyl 4-(4-chloro-6-ethyl-thieno-[2,3-d]-pyrimidin-2-yl)-benzoate;
from 2-amino-5-propyl-3-ethoxycarbonyl-thiophene
methyl 4-(4-chloro-6-propyl-thieno-[2,3-d]-pyrimidin-2-yl)-benzoate;
from 2-amino-5-chloro-3-ethoxycarbonyl-thiophene
methyl 4-(4-chloro-6-chloro-thieno-[2,3-d]-pyrimidin-2-yl)-benzoate;
from 2-amino-4-chloro-5-methyl-3-ethoxycarbonyl-thiophene
methyl 4-(4-chloro-5-chloro-6-methyl-thieno-[2,3-d]-pyrimidin-2-yl)-benzoate;
from 2-amino-5-nitro-3-ethoxycarbonyl-thiophene
methyl 4-(4-chloro-6-nitro-thieno-[2,3-d]-pyrimidin-2-yl)-benzoate;
from 2-amino-4,5-dimethyl-3-ethoxycarbonyl-thiophene
methyl 4-(4-chloro-5,6-dimethyl-thieno-[2,3-d]-pyrimidin-2-yl)-benzoate;
from 2-amino-5-trifluoromethyl-3-ethoxycarbonyl-thiophene
methyl 4-(4-chloro-6-trifluoromethyl-thieno-[2,3-d]-pyrimidin-2-yl)-benzoate,
are obtained.

EXAMPLE 5

Analogous to Example 1, by reaction of 3,4-methylenedioxy-benzylamine
with methyl 4-(4-chloro-6-methyl-thieno-[2,3-d]-pyrimidin-2-yl)-benzoate,
methyl 4-[4-(3,4-methylenedioxybenzylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate,
methyl 4-[4-(3,4-methylenedioxybenzylamino)-5-methyl-thieno-[2,3-d]-pyrimidin-2-yl]-benzoate;
with methyl 4-(4-chloro-5,6,7,8-tetrahydro-[1]-benzothieno-[2,3-d]-pyrimidin-2-yl)-benzoate,
methyl 4-[4-(3,4-methylenedioxybenzylamino)-5,6,7,8-tetrahydro-[1]-benzothieno-[2,3-d]-pyrimidin-2-yl]-benzoate, m.p. 198°;
with methyl 4-(4-chloro-5,6-cyclopenteno-thieno-[2,3-d]-pyrimidin-2-yl)-benzoate,
methyl 4-[4-(3,4-methylenedioxybenzylamino)-5,6-cylcopenteno-thieno-[2,3-d]-pyrimidin-2-yl]-benzoate;
with methyl 4-(4-chloro-5,6-cyclohepteno-thieno-[2,3-d]-pyrimidin-2-yl)-benzoate,
methyl 4-[4-(3,4-methylenedioxybenzylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate,
methyl 4-[4-(3,4-methylenedioxybenzylamino)-6-ethyl-thieno-[2,3-d]-pyrimidin-2-yl]-benzoate;
with methyl 4-(4-chloro-6-propyl-thieno-[2,3-d]-pyrimidin-2-yl)-benzoate,
methyl 4-[4-(3,4-methylenedioxybenzylamino)-6-propyl-thieno-[2,3-d]-pyrimidin-2-yl]-benzoate;
with methyl 4-(4-chloro-6-chloro-thieno-[2,3-d]-pyrimidin-2-yl)-benzoate,
methyl 4-[4-(3,4-methylenedioxybenzylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate,
methyl 4-[4-(3,4-methylenedioxybenzylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate,
methyl 4-[4-(3,4-methylenedioxybenzylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate,
methyl 4-[4-(3,4-methylenedioxybenzylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate,
methyl 4-[4-(3,4-methylenedioxybenzylamino)-6-trifluoromethyl-thieno-[2,3-d]-pyrimidin-2-yl]-benzoate,
are obtained.

Analogously, by reaction of 3-chloro-4-methoxybenzylamine
with methyl 4-(4-chloro-6-methyl-thieno-[2,3-d]-pyrimidin-2-yl)-benzoate,
methyl 4-[4-(3-chloro-4-methoxybenzylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate,
methyl 4-[4-(3-chloro-4-methoxybenzylamino)-5-methyl-thieno-[2,3-d]-pyrimidin-2-yl]-benzoate;
with methyl 4-(4-chloro-5,6,7,8-tetrahydro-[1]-benzothieno-[2,3-d]-pyrimidin-2-yl)-benzoate,
methyl 4-[4-(3-chloro-4-methoxybenzylamino)-5,6,7,8-tetrahydro-[1]-benzothieno-[2,3-d]-pyrimidin-2-yl]-benzoate;
with methyl 4-(4-chloro-5,6-cyclopenteno-thieno-[2,3-d]-pyrimidin-2-yl)-benzoate,
methyl 4-[4-(3-chloro-4-methoxybenzylamino)-5,6-cylcopenteno-thieno-[2,3-d]-pyrimidin-2-yl]-benzoate;
with methyl 4-(4-chloro-5,6-cyclohepteno-thieno-[2,3-d]-pyrimidin-2-yl)-benzoate,
methyl 4-[4-(3-chloro-4-methoxybenzylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate,
methyl 4-[4-(3-chloro-4-methoxybenzylamino)-6-ethyl-thieno-[2,3-d]-pyrimidin-2-yl]-benzoate;
with methyl 4-(4-chloro-6-chloro-thieno-[2,3-d]-pyrimidin-2-yl)-benzoate,
methyl 4-[4-(3-chloro-4-methoxybenzylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate,
methyl 4-[4-(3-chloro-4-methoxybenzylamino)-5-choro-6-methyl-thieno-[2,3-d]-pyrimidin-2-yl]-benzoate;
with methyl 4-(4-chloro-6-nitro-thieno-[2,3-d]-pyrimidin-2-yl)-benzoate,
methyl 4-[4-(3-chloro-4-methoxybenzylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate,
methyl 4-[4-(3-chloro-4-methoxybenzylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate,
methyl 4-[4-(3-chloro-4-methoxybenzylamino)-6-trifluoromethyl-thieno-[2,3-d]-pyrimidin-2-yl]-benzoate,
are obtained.

Analogously, by reaction of 3,4-dimethoxy-benzylamine
with methyl 4-(4-chloro-6-methyl-thieno-[2,3-d]-pyrimidin-2-yl)-benzoate,
methyl 4-[4-(3,4-dimethoxybenzylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate,
methyl 4-[4-(3,4-dimethoxybenzylamino)-5-methyl-thieno-[2,3-d]-pyrimidin-2-yl]-benzoate;

with methyl 4-(4-chloro-5,6,7,8-tetrahydro-[1]-benzothieno-[2,3-d]-pyrimidin-2-yl)-benzoate,
methyl 4-[4-(3,4-dimethoxybenzylamino)-5,6,7,8-tetrahydro-[1]-benzothieno-[2,3-d]-pyrimidin-2-yl]-benzoate;
with methyl 4-(4-chloro-5,6-cyclopenteno-thieno-[2,3-d]-pyrimidin-2-yl)-benzoate,
methyl 4-[4-(3,4-dimethoxybenzylamino)-5,6-cylcopenteno-thieno-[2,3-d]-pyrimidin-2-yl]-benzoate;
with methyl 4-(4-chloro-5,6-cyclohepteno-thieno-[2,3-d]-pyrimidin-2-yl)-benzoate,
methyl 4-[4-(3,4-dimethoxybenzylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate,
methyl 4-[4-(3,4-dimethoxybenzylamino)-6-ethyl-thieno-[2,3-d]-pyrimidin-2-yl]-benzoate;
with methyl 4-(4-chloro-6-chloro-thieno-[2,3-d]-pyrimidin-2-yl)-benzoate,
methyl 4-[4-(3,4-dimethoxybenzylamino)-6-chloro-thieno-[2,3-d]-pyrimidin-2-yl)-benzoate;
with methyl 4-(4-chloro-5-chloro-6-methyl-thieno-[2,3-d]-pyrimidin-2-yl)-benzoate,
methyl 4-[4-(3,4-dimethoxybenzylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate,
methyl 4-[4-(3,4-dimethoxybenzylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate,
methyl 4-[4-(3,4-dimethoxybenzylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate,
methyl 4-[4-(3,4-dimethoxybenzylamino)-6-trifluoromethyl-thieno-[2,3-d]-pyrimidin-2-yl)-benzoate,
are obtained.

Analogously, by reaction of benzylamine
with methyl 4-(4-chloro-6-methyl-thieno-[2,3-d]-pyrimidin-2-yl)-benzoate,
methyl 4-(4-benzylamino-6-methyl-thieno-[2,3-d]-pyrimidin-2-yl)-benzoate;
with methyl 4-(4-chloro-5-methyl-thieno-[2,3-d]-pyrimidin-2-yl)-benzoate,
methyl 4-(4-benzylamino-5-methyl-thieno-[2,3-d]-pyrimidin-2-yl)-benzoate;
with methyl 4-(4-chloro-5,6,7,8-tetrahydro-[1]-benzothieno-[2,3-d]-pyrimidin-2-yl)-benzoate,
methyl 4-(4-benzylamino-5,6,7,8-tetrahydro-[1]-benzothieno-[2,3-d]-pyrimidin-2-yl)-benzoate;
with methyl 4-(4-chloro-5,6-cyclopenteno-thieno-[2,3-d]-pyrimidin-2-yl)-benzoate,
methyl 4-(4-benzylamino-5,6-cylcopenteno-thieno-[2,3-d]-pyrimidin-2-yl)-benzoate;
with methyl 4-(4-chloro-5,6-cyclohepteno-thieno-[2,3-d]-pyrimidin-2-yl)-benzoate,
methyl 4-(4-benzylamino-5,6-cyclohepteno-thieno-[2,3-d]-pyrimidin-2-yl)-benzoate;
with methyl 4-(4-chloro-6-ethyl-thieno-[2,3-d]-pyrimidin-2-yl)-benzoate,
methyl 4-(4-benzylamino-6-ethyl-thieno-[2,3-d]-pyrimidin-2-yl)-benzoate;
with methyl 4-(4-chloro-6-chloro-thieno-[2,3-d]-pyrimidin-2-yl)-benzoate,
methyl 4-(4-benzylamino-6-chloro-thieno-[2,3-d]-pyrimidin-2-yl)-benzoate;
with methyl 4-(4-chloro-5-chloro-6-methyl-thieno-[2,3-d]-pyrimidin-2-yl)-benzoate,
methyl 4-(4-benzylamino-5-chloro-6-methyl-thieno-[2,3-d]-pyrimidin-2-yl)-benzoate;
with methyl 4-(4-chloro-6-nitro-thieno-[2,3-d]-pyrimidin-2-yl)-benzoate,
methyl 4-(4-benzylamino-6-nitro-thieno-[2,3-d]-pyrimidin-2-yl)-benzoate;
with methyl 4-(4-chloro-5,6-dimethyl-thieno-[2,3-d]-pyrimidin-2-yl)-benzoate,
methyl 4-(4-benzylamino-5,6-dimethyl-thieno-[2,3-d]-pyrimidin-2-yl)-benzoate;
with methyl 4-(4-chloro-6-trifluoromethyl-thieno-[2,3-d]-pyrimidin-2-yl)-benzoate,
methyl 4-(4-benzylamino-6-trifluoromethyl-thieno-[2,3-d]-pyrimidin-2-yl)-benzoate,
are obtained.

Analogously, by reaction of 4-fluorobenzylamine
with methyl 4-(4-chloro-6-methyl-thieno-[2,3-d]-pyrimidin-2-yl)-benzoate
methyl 4-[4-(4-fluorobenzylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate
methyl 4-[4-(4-fluorobenzylamino)-5-methyl-thieno-[2,3-d]-pyrimidin-2-yl]-benzoate;
with methyl 4-(4-chloro-5,6,7,8-tetrahydro-[1]-benzothieno-[2,3-d]-pyrimidin-2-yl)-benzoate
methyl 4-[4-(4-fluorobenzylamino)-5,6,7,8-tetrahydro-[1]-benzothieno-[2,3-d]-pyrimidin-2-yl]-benzoate;
with methyl 4-(4-chloro-5,6-cyclo-penteno-thieno-[2,3-d]-pyrimidin-2-yl)-benzoate
methyl 4-[4-(4-fluorobenzylamino)-5,6-cylcopenteno-thieno-[2,3-d]-pyrimidin-2-yl]-benzoate;
with methyl 4-(4-chloro-5,6-cyclohepteno-thieno-[2,3-d]-pyrimidin-2-yl)-benzoate
methyl 4-[4-(4-fluorobenzylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate
methyl 4-[4-(4-fluorobenzylamino)-6-ethyl-thieno-[2,3-d]-pyrimidin-2-yl]-benzoate;
with methyl 4-(4-chloro-6-chloro-thieno-[2,3-d]-pyrimidin-2-yl)-benzoate
methyl 4-[4-(4-fluorobenzylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate
methyl 4-[4-(4-fluorobenzylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate
methyl 4-[4-(4-fluorobenzylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate
methyl 4-[4-(4-fluorobenzylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate
methyl 4-[4-(4-fluorobenzylamino)-6-trifluoromethyl-thieno-[2,3-d]-pyrimidin-2-yl]-benzoate,
are obtained.

Analogously, by reaction of 3,4-dichlorobenzylamine
with methyl 4-(4-chloro-6-methyl-thieno-(2,3-d]-pyrimidin-2-yl)-benzoate
methyl 4-[4-(3,4-dichlorobenzylamino)-6-methyl-thieno-[2,3-d]-pyrimidin-2-yl]-benzoate;

with methyl 4-(4-chloro-5-methyl-thieno-[2,3-d]-pyrimidin-2-yl)-benzoate
methyl 4-[4-(3,4-dichlorobenzylamino)-5-methyl-thieno-[2,3-d]-pyrimidin-2-yl]-benzoate;
with methyl 4-(4-chloro-5,6,7,8-tetrahydro-1]-benzothieno-[2,3-d]-pyrimidin-2-yl)-benzoate
methyl 4-[4-(3,4-dichlorobenzylamino)-5,6,7,8-tetrahydro-[1]-benzothieno-[2,3-d]-pyrimidin-2-yl]-benzoate;
with methyl 4-(4-chloro-5,6-cyclopenteno-thieno-(2,3-d]-pyrimidin-2-yl)-benzoate
methyl 4-[4-(3,4-dichlorobenzylamino)-5,6-cylco-penteno-thieno-[2,3-d]-pyrimidin-2-yl]-benzoate;
with methyl 4-(4-chloro-5,6-cyclohepteno-thieno-[2,3-d]-pyrimidin-2-yl)-benzoate
methyl 4-[4-(3,4-dichlorobenzylamino)-5,6-cyclo-hepteno-thieno-[2,3-d]-pyrimidin-2-yl]-benzoate;
with methyl 4-(4-chloro-6-ethyl-thieno-[2,3-d]-pyrimidin-2-yl)-benzoate
methyl 4-[4-(3,4-dichlorobenzylamino)-6-ethyl-thieno-[2,3-d]-pyrimidin-2-yl]-benzoate;
with methyl 4-(4-chloro-6-chloro-thieno-[2,3-d]-pyrimidin-2-yl)-benzoate
methyl 4-[4-(3,4-dichlorobenzylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate
methyl 4-[4-(3,4-dichlorobenzylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate
methyl 4-[4-(3,4-dichlorobenzylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate
methyl 4-[4-(3,4-dichlorobenzylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate
methyl 4-[4-(3,4-dichlorobenzylamino)-6-trifluoro-methyl-thieno-[2,3-d]-pyrimidin-2-yl]-benzoate,
are obtained Analogously, by reaction of 3-nitrobenzylamine
with methyl 4-(4-chloro-6-methyl-thieno-[2,3-d]-pyrimidin-2-yl)-benzoate
methyl 4-[4-(3-nitrobenzylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate
methyl 4-[4-(3-nitrobenzylamino)-5-methyl-thieno-[2,3-d]-pyrimidin-2-yl]-benzoate;
with methyl 4-(4-chloro-5,6,7,8-tetrahydro-[1]-benzothieno-[2,3-d]-pyrimidin-2-yl)-benzoate
methyl 4-[4-(3-nitrobenzylamino)-5,6,7,8-tetrahydro-[1]-benzothieno-[2,3-d]-pyrimidin-2-yl]-benzoate;
with methyl 4-(4-chloro-5,6-cyclopenteno-thieno-[2,3-d]-pyrimidin-2-yl)-benzoate
methyl 4-[4-(3-nitrobenzylamino)-5,6-cyclo-penteno-thieno-[2,3-d]-pyrimidin-2-yl]-benzoate;
with methyl 4-(4-chloro-5,6-cyclohepteno-thieno-[2,3-d]-pyrimidin-2-yl)-benzoate
methyl 4-[4-(3-nitrobenzylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate
methyl 4-[4-(3-nitrobenzylamino)-6-ethyl-thieno-[2,3-d]-pyrimidin-2-yl]-benzoate;
with methyl 4-(4-chloro-6-chloro-thieno-[2,3-d]-pyrimidin-2-yl)-benzoate
methyl 4-[4-(3-nitrobenzylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate
methyl 4-[4-(3-nitrobenzylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate
methyl 4-[4-(3-nitrobenzylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate
methyl 4-[4-(3-nitrobenzylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate
methyl 4-[4-(3-nitrobenzylamino)-6-trifluoro-methyl-thieno-[2,3-d]-pyrimidin-2-yl]-benzoate,
are obtained.

Analogously, by reaction of 3,4-methylenedioxyphenethylamine
with methyl 4-(4-chloro-6-methyl-thieno-[2,3-d]-pyrimidin-2-yl)-benzoate
methyl 4-[4-(3,4-methylenedioxyphenethylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate
methyl 4-[4-(3,4-methylenedioxyphenethylamino)-5-methyl-thieno-[2,3-d]-pyrimidin-2-yl]-benzoate;
with methyl 4-(4-chloro-5,6,7,8-tetrahydro-[1]-benzothieno-[2,3-d]-pyrimidin-2-yl)-benzoate
methyl 4-[4-(3,4-methylenedioxyphenethylamino)-5,6,7,8-tetrahydro-[1]-benzothieno-[2,3-d]-pyrimidin-2-yl]-benzoate;
with methyl 4-(4-chloro-5,6-cyclopenteno-thieno-[2,3-d]-pyrimidin-2-yl)-benzoate
methyl 4-[4-(3,4-methylenedioxyphenethylamino)-5,6-cyclo-penteno-thieno-[2,3-d]-pyrimidin-2-yl]-benzoate;
with methyl 4-(4-chloro-5,6-cyclohepteno-thieno-[2,3-d]-pyrimidin-2-yl)-benzoate
methyl 4-[4-(3,4-methylenedioxyphenethylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate
methyl 4-[4-(3,4-methylenedioxyphenethylamino)-6-ethyl-thieno-[2,3-d]-pyrimidin-2-yl]-benzoate;
with methyl 4-(4-chloro-6-chloro-thieno-[2,3-d]-pyrimidin-2-yl)-benzoate
methyl 4-[4-(3,4-methylenedioxyphenethylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate
methyl 4-[4-(3,4-methylenedioxyphenethylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate
methyl 4-[4-(3,4-methylenedioxyphenethylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate
methyl 4-[4-(3,4-methylenedioxyphenethylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate methyl 4-[4-(3,4-methylenedioxyphenethylamino)-6-trifluoro-methyl-thieno-[2,3-d]-pyrimidin-2-yl]-benzoate, are obtained.

Analogously, by reaction of 3,4-ethylenedioxybenzylamine
with methyl 4-(4-chloro-6-methyl-thieno-[2,3-d]-pyrimidin-2-yl)-benzoate
methyl 4-[4-(3,4-ethylenedioxyphenethylamino)-6-methyl-thieno-[2,3-d]-pyrimidin-2-yl]-benzoate;
with methyl 4-(4-chloro-5-methyl-thieno-[2,3-d]-pyrimidin-2-yl)-benzoate
methyl 4-[4-(3,4-ethylenedioxyphenethylamino)-5-methyl-thieno-[2,3-d]-pyrimidin-2-yl]-benzoate;
with methyl 4-(4-chloro-5,6,7,8-tetrahydro-[1]-benzothieno-[2,3-d]-pyrimidin-2-yl)-benzoate
methyl 4-[4-(3,4-ethylenedioxyphenethylamino)-5,6,7,8-tetrahydro-[(1-benzothieno-[2,3-d]-pyrimidin-2-yl]-benzoate;
with methyl 4-(4-chloro-5,6-cyclopenteno-thieno-[2,3-d]-pyrimidin-2-yl)-benzoate
methyl 4-[4-(3,4-ethylenedioxyphenethylamino)-5,6-cyclopenteno-thieno-[2,3-d]-pyrimidin-2-yl]-benzoate;
with methyl 4-(4-chloro-5,6-cyclohepteno-thieno-[2,3-d]-pyrimidin-2-yl)-benzoate
methyl 4-[4-(3,4-ethylenedioxyohenethylamino)-5,6-cyclohepteno-thieno-[2,3-d]-pyrimidin-2-yl]-benzoate;
with methyl 4-(4-chloro-6-ethyl-thieno-[2,3-d]-pyrimidin-2-yl)-benzoate
methyl 4-[4-(3,4-ethylenedioxyphenethylamino)-6-ethyl-thieno-[2,3-d]-pyrimidin-2-yl]-benzoate;
with methyl 4-(4-chloro-6-chloro-thieno-(2,3-d]-pyrimidin-2-yl)-benzoate
methyl 4-[4-(3,4-ethylenedioxyphenethylamino)-6-chloro-thieno-[2,3-d]-pyrimidin-2-yl]-benzoate;
with methyl 4-(4-chloro-5-chloro-6-methyl-thieno-[2,3-d]-pyrimidin-2-yl)-benzoate
methyl 4-[4-(3,4-ethylenedioxyphenethylamino)-5-chloro-6-methyl-thieno-[2,3-d]-pyrimidin-2-yl]-benzoate;
with methyl 4-(4-chloro-6-nitro-thieno-[2,3-d]-pyrimidin-2-yl)-benzoate
methyl 4-[4-(3,4-ethylenedioxyphenethylamino)-6-nitro-thieno-[2,3-d]-pyrimidin-2-yl]-benzoate;
with methyl 4-(4-chloro-5,6-dimethyl-thieno-[2,3-d]-pyrimidin-2-yl)-benzoate
methyl 4-[4-(3,4-ethylenedioxyphenethylamino)-5,6-dimethyl-thieno-[2,3-d]-pyrimidin-2-yl]-benzoate;
with methyl 4-(4-chloro-6-trifluoromethyl-thieno-[2,3-d]-pyrimidin-2-yl)-benzoate
methyl 4-[4-(3,4-ethylenedioxyphenethylamino)-6-trifluoromethyl-thieno-[2,3-d]-pyrimidin-2-yl]-benzoate, are obtained.

Analogously, by reaction of phenethylamine
with methyl 4-(4-chloro-6-methyl-thieno-[2,3-d]-pyrimidin-2-yl)-benzoate
methyl 4-(4-phenethylamino-6-methyl-thieno-[2,3-d]-pyrimidin-2-yl)-benzoate;
with methyl 4-(4-chloro-5-methyl-thieno-[2,3-d]-pyrimidin-2-yl)-benzoate
methyl 4-(4-phenethylamino-5-methyl-thieno-[2,3-d]-pyrimidin-2-yl)-benzoate;
with methyl 4-(4-chloro-5,6,7,8-tetrahydro-[1]-benzothieno-[2,3-d]-pyrimidin-2-yl)-benzoate
methyl 4-(4-phenethylamino-5,6,7,8-tetrahydro-[1]-benzothieno-[2,3-d]-pyrimidin-2-yl)-benzoate;
with methyl 4-(4-chloro-5,6-cyclopenteno-thieno-[2,3-d]-pyrimidin-2-yl)-benzoate
methyl 4-(4-phenethylamino-5,6-cyclo-penteno-thieno-[2,3-d]-pyrimidin-2-yl)-benzoate;
with methyl 4-(4-chloro-5,6-cyclohepteno-thieno-[2,3-d]-pyrimidin-2-yl)-benzoate
methyl 4-(4-phenethylamino-5,6-cyclohepteno-thieno-[2,3-d]-pyrimidin-2-yl)-benzoate;
with methyl 4-(4-chloro-6-ethyl-thieno-[2,3-d]-pyrimidin-2-yl)-benzoate
methyl 4-(4-phenethylamino-6-ethyl-thieno-[2,3-d]-pyrimidin-2-yl)-benzoate;
with methyl 4-(4-chloro-6-chloro-thieno-[2,3-d]-pyrimidin-2-yl)-benzoate
methyl 4-(4-phenethylamino-6-chloro-thieno-[2,3-d]-pyrimidin-2-yl)-benzoate;
with methyl 4-(4-chloro-5-chloro-6-methyl-thieno-[2,3-d]-pyrimidin-2-yl)-benzoate
methyl 4-(4-phenethylamino-5-chloro-6-methyl-thieno-[2,3-d]-pyrimidin-2-yl)-benzoate;
with methyl 4-(4-chloro-6-nitro-thieno-[2,3-d]-pyrimidin-2-yl)-benzoate
methyl 4-(4-phenethylamino-6-nitro-thieno-[2,3-d]-pyrimidin-2-yl)-benzoate;
with methyl 4-(4-chloro-5,6-dimethyl-thieno-[2,3-d]-pyrimidin-2-yl)-benzoate
methyl 4-(4-phenethylamino-5,6-dimethyl-thieno-[2,3-d]-pyrimidin-2-yl)-benzoate;
with methyl 4-(4-chloro-6-trifluoromethyl-thieno-[2,3-d]-pyrimidin-2-yl)-benzoate
methyl 4-(4-phenethylamino-6-trifluoro-methyl-thieno-[2,3-d]-pyrimidin-2-yl)-benzoate,
are obtained.

EXAMPLE 6

A solution of 1.1 g of methyl 4-[4-(3,4-methylenedioxybenzylamino)-6-methyl-thieno-[2,3-d]-pyrimidin-2-yl]-benzoate, 30 ml of 2N NaOH and 30 ml of tetrahydrofuran is heated at 100° for 6 hours. After cooling and acidification of the solution with 20% HCl, the mixture is further worked up in the customary manner. 0.75 g of 4-[4-(3,4-methylenedioxybenzylamino)-6-methyl-thieno-[2,3-d]-pyrimidin-2-yl]-benzoic acid is obtained, m.p. >250°.

Analogously, the following carboxylic acids are obtained from the esters obtained in Example 5
4-[4-(3,4-methylenedioxybenzyl)-5-methyl-thieno-[2,3-d]-pyrimidin-2-yl]-benzoic acid;
4-[4-(3,4-methylenedioxybenzylamino)-5,6,7,8-tetrahydro-[1]-benzothieno-[2,3-d]-pyrimidin-2-yl]-benzoic acid, dihydrate, m.p. 249°, sodium salt, m.p. >250°;
4-[4-(3,4-methylenedioxybenzylamino)-5,6-cyclo-penteno-thieno-[2,3-d]-pyrimidin-2-yl]-benzoic acid;
4-[4-(3,4-methylenedioxybenzylamino)-5,6-cyclo-hepteno-thieno-[2,3-d]-pyrimidin-2-yl]-benzoic acid;
4-[4-(3,4-methylenedioxybenzylamino)-6-ethyl-thieno-[2,3-d]-pyrimidin-2-yl]-benzoic acid, m.p. 189°;
4-[4-(3,4-methylenedioxybenzylamino)-6-propyl-thieno-[2,3-d]-pyrimidin-2-yl]-benzoic acid;
4-[4-(3,4-methylenedioxybenzylamino)-6-chloro-thieno-[2,3-d]-pyrimidin-2-yl]-benzoic acid, m.p. >250°;
4-[4-(3,4-methylenedioxybenzylamino)-5-chloro-6-methyl-thieno-[2,3-d]-pyrimidin-2-yl]-benzoic acid, m.p. >250°;
4-[4-(3,4-methylenedioxybenzylamino)-6-nitro-thieno-[2,3-d]-pyrimidin-2-yl]-benzoic acid;
4-[4-(3,4-methylenedioxybenzylamino)-5,6-dimethyl-thieno-[2,3-d]-pyrimidin-2-yl]-benzoic acid, m.p. 172°;
4-[4-(3,4-methylenedioxybenzylamino)-6-trifluoro-methyl-thieno-[2,3-d]-pyrimidin-2-yl]-benzoic acid;
4-[4-(3-chloro-4-methoxybenzylamino)-6-methyl-thieno-[2,3-d]-pyrimidin-2-yl]-benzoic acid;

4-[4-(3-chloro-4-methoxybenzylamino)-5-methyl-thieno-[2,3-d]-pyrimidin-2-yl]-benzoic acid;
4-[4-(3-chloro-4-methoxybenzylamino)-5,6,7,8-tetrahydro-[1]-benzothieno-[2,3-d]-pyrimidin-2-yl]-benzoic acid, m.p. 245°;
4-[4-(3-chloro-4-methoxybenzylamino)-5,6-cyclo-penteno-thieno-[2,3-d]-pyrimidin-2-yl]-benzoic acid;
4-[4-(3-chloro-4-methoxybenzylamino)-5,6-cyclo-hepteno-thieno-[2,3-d]-pyrimidin-2-yl]-benzoic acid;
4-[4-(3-chloro-4-methoxybenzylamino)-6-ethyl-thieno-[2,3-d]-pyrimidin-2-yl]-benzoic acid, m.p. 257°;
4-[4-(3-chloro-4-methoxybenzylamino)-6-chloro-thieno-[2,3-d]-pyrimidin-2-yl]-benzoic acid, m.p. >250°;
4-[4-(3-chloro-4-methoxybenzylamino)-5-chloro-6-methyl-thieno-[2,3-d]-pyrimidin-2-yl]-benzoic acid, sodium salt, m.p. >250°;
4-[4-(3-chloro-4-methoxybenzylamino)-6-nitro-thieno-[2,3-d]-pyrimidin-2-yl]-benzoic acid;
4-[4-(3-chloro-4-methoxybenzylamino) -5,6-dimethyl-thieno-[2,3-d]-pyrimidin-2-yl]-benzoic acid;
4-[4-(3-chloro-4-methoxybenzylamino)-6-trifluoro-methyl-thieno-[2,3-d]-pyrimidin-2-yl]-benzoic acid;
4-[4-(3,4-dimethoxybenzylamino)-6-methyl-thieno-[2,3-d]-pyrimidin-2-yl]-benzoic acid;
4-[4-(3,4-dimethoxybenzylamino)-5-methyl-thieno-[2,3-d]-pyrimidin-2-yl]-benzoic acid;
4-[4-(3,4-dimethoxybenzylamino)-5,6,7,8-tetrahydro-[1]-benzothieno-[2,3-d]-pyrimidin-2-yl]-benzoic acid;
4-[4-(3,4-dimethoxybenzylamino)-5,6-cyclo-penteno-thieno-[2,3-d]-pyrimidin-2-yl]-benzoic acid;
4-[4-(3,4-dimethoxybenzylamino)-5,6-cyclo-hepteno-thieno-[2,3-d]-pyrimidin-2-yl]-benzoic acid;
4-[4-(3,4-dimethoxybenzylamino)-6-ethyl-thieno-[2,3-d]-pyrimidin-2-yl]-benzoic acid;
4-[4-(3,4-dimethoxybenzylamino)-6-chloro-thieno-[2,3-d]-pyrimidin-2-yl]-benzoic acid;
4-[4-(3,4-dimethoxybenzylamino)-5-chloro-6-methyl-thieno-[2,3-d]-pyrimidin-2-yl]-benzoic acid;
4-[4-(3,4-dimethoxybenzylamino)-6-nitro-thieno-[2,3-d]-pyrimidin-2-yl]-benzoic acid;
4-[4-(3,4-dimethoxybenzylamino)-5,6-dimethyl-thieno-[2,3-d]-pyrimidin-2-yl]-benzoic acid;
4-[4-(3,4-dimethoxybenzylamino)-6-trifluoro-methyl-thieno-[2,3-d]-pyrimidin-2-yl]-benzoic acid;
4-(4-benzylamino-6-methyl-thieno-[2,3-d]-pyrimidin-2-yl)-benzoic acid, m.p. >250°;
4-(4-benzylamino-5-methyl-thieno-[2,3-d]-pyrimidin-2-yl)-benzoic acid;
4-(4-benzylamino-5,6,7,8-tetrahydro-[1]-benzo-thieno-[2,3-d]-pyrimidin-2-yl)-benzoic acid, m.p >270°;
4-(4-benzylamino-5,6-cyclopenteno-thieno-[2,3-d]-pyrimidin-2-yl)-benzoic acid;
4-(4-benzylamino-5,6-cyclohepteno-thieno-[2,3-d]-pyrimidin-2-yl)-benzoic acid;
4-(4-benzylamino-6-ethyl-thieno-[2,3-d]-pyrimidin-2-yl)-benzoic acid, m.p. 172°;
4-(4-benzylamino-6-chloro-thieno-[2,3-d]-pyrimidin-2-yl)-benzoic acid;
4-(4-benzylamino-5-chloro-6-methyl-thieno-[2,3-d]-pyrimidin-2-yl)-benzoic acid;
4-(4-benzylamino-6-nitro-thieno-[2,3-d]-pyrimidin-2-yl)-benzoic acid;
4-(4-benzylamino-5,6-dimethyl-thieno-[2,3-d]-pyrimidin-2-yl)-benzoic acid;
4-(4-benzylamino-6-trifluoro-methyl-thieno-[2,3-d]-pyrimidin-2-yl)-benzoic acid;
4-(4-fluorobenzylamino)-6-methyl-thieno-[2,3-d]-pyrimidin-2-yl]-benzoic acid;
4-[4-(4-fluorobenzylamino)-5-methyl-thieno-[2,3-d]-pyrimidin-2-yl]-benzoic acid;
4-[4-(4-fluorobenzylamino)-5,6,7,8-tetrahydro-[1]-benzothieno-[2,3-d]-pyrimidin-2-yl]-benzoic acid;
4-[4-(4-fluorobenzylamino)-5,6-cyclopenteno-thieno-[2,3-d]-pyrimidin-2-yl]-benzoic acid;
4-[4-(4-fluorobenzylamino)-5,6-cyclohepteno-thieno-[2,3-d]-pyrimidin-2-yl]-benzoic acid;
4-[4-(4-fluorobenzylamino)-6-ethyl-thieno-[2,3-d]-pyrimidin-2-yl]-benzoic acid;
4-[4-(4-fluorobenzylamino)-6-chloro-thieno-[2,3-d]-pyrimidin-2-yl]-benzoic acid;
4-[4-(4-fluorobenzylamino)-5-chloro-6-methyl-thieno-[2,3-d]-pyrimidin-2-yl]-benzoic acid;
4-[4-(4-fluorobenzylamino)-6-nitro-thieno-[2,3-d]-pyrimidin-2-yl]-benzoic acid;
4-[4-(4-fluorobenzylamino)-5,6-dimethyl-thieno-[2,3-d]-pyrimidin-2-yl]-benzoic acid;
4-[4-(4-fluorobenzylamino)-6-trifluoro-methyl-thieno-[2,3-d]-pyrimidin-2-yl]-benzoic acid;
4-[4-(3,4-dichlorobenzylamino)-6-methyl-thieno-[2,3-d]-pyrimidin-2-yl]-benzoic acid;
4-[4-(3,4-dichlorobenzylamino)-5-methyl-thieno-[2,3-d]-pyrimidin-2-yl]-benzoic acid;
4-[4-(3,4-dichlorobenzylamino)-5,6,7,8-tetrahydro-[1]-benzothieno-[2,3-d]-pyrimidin-2-yl]-benzoic acid;
4-[4-(3,4-dichlorobenzylamino)-5,6-cyclopenteno-thieno-[2,3-d]-pyrimidin-2-yl]-benzoic acid;
4-[4-(3,4-dichlorobenzylamino)-5,6-cyclohepteno-thieno-(2,3-d]-pyrimidin-2-yl]-benzoic acid;
4-[4-(3,4-dichlorobenzylamino)-6-ethyl-thieno-[2,3-d]-pyrimidin-2-yl]-benzoic acid;
4-[4-(3,4-dichlorobenzylamino)-6-chloro-thieno-[2,3-d]-pyrimidin-2-yl]-benzoic acid;
4-[4-(3,4-dichlorobenzylamino)-5-chloro-6-methyl-thieno-[2,3-d]-pyrimidin-2-yl]-benzoic acid;
4-[4-(3,4-dichlorobenzylamino)-6-nitro-thieno-[2,3-d]-pyrimidin-2-yl]-benzoic acid;
4-[4-(3,4-dichlorobenzylamino)-5,6-dimethyl-thieno-[2,3-d]-pyrimidin-2-yl]-benzoic acid;
4-[4-(3,4-dichlorobenzylamino)-6-trifluoro-methyl-thieno-[2,3-d]-pyrimidin-2-yl]-benzoic acid;
4-[4-(3-nitrobenzylamino)-6-methyl-thieno-[2,3-d]-pyrimidin-2-yl]-benzoic acid;
4-[4-(3-nitrobenzylamino)-5-methyl-thieno-[2,3-d]-pyrimidin-2-yl]-benzoic acid;
4-[4-(3-nitrobenzylamino)-5,6,7,8-tetrahydro-[1-benzothieno-[2,3-d]-pyrimidin-2-yl]-benzoic acid;
4-[4-(3-nitrobenzylamino)-5,6-cyclopenteno-thieno-[2,3-d]-pyrimidin-2-yl]-benzoic acid;
4-[4-(3-nitrobenzylamino)-5,6-cyclohepteno-thieno-[2,3-d]-pyrimidin-2-yl]-benzoic acid;
4-[4-(3-nitrobenzylamino)-6-ethyl-thieno-[2,3-d]-pyrimidin-2-yl]-benzoic acid;
4-[4-(3-nitrobenzylamino)-6-chloro-thieno-[2,3-d]-pyrimidin-2-yl]-benzoic acid;
4-[4-(3-nitrobenzylamino)-5-chloro-6-methyl-thieno-[2,3-d]-pyrimidin-2-yl]-benzoic acid;
4-[4-(3-nitrobenzylamino)-6-nitro-thieno-[2,3-d]-pyrimidin-2-yl]-benzoic acid;
4-[4-(3-nitrobenzylamino)-5,6-dimethyl-thieno-[2,3-d]-pyrimidin-2-yl]-benzoic acid;
4-[4-(3-nitrobenzylamino)-6-trifluoro-methyl-thieno-[2,3-d]-pyrimidin-2-yl]-benzoic acid;
4-(4-(3,4-methylenedioxyphenethylamino)-6-methyl-thieno-[2,3-d]-pyrimidin-2-yl]-benzoic acid;
4-[4-(3,4-methylenedioxyphenethylamino)-5-methyl-thieno-[2,3-d]-pyrimidin-2-yl]-benzoic acid;

4-[4-(3,4-methylenedioxyphenethylamino)-5,6,7,8-tetrahydro-[1]-benzothieno-[2,3-d]-pyrimidin-2-yl]-benzoic acid;
4-[4-(3,4-methylenedioxyphenethylamino)-5,6-cyclopenteno-thieno-[2,3-d]-pyrimidin-2-yl]-benzoic acid;
4-[4-(3,4-methylenedioxyphenethylamino)-5,6-cyclohepteno-thieno-[2,3-d]-pyrimidin-2-yl]-benzoic acid;
4-[4-(3,4-methylenedioxyphenethylamino)-6-ethyl-thieno-[2,3-d]-pyrimidin-2-yl]-benzoic acid;
4-[4-(3,4-methylenedioxyphenethylamino)-6-chloro-thieno-[2,3-d]-pyrimidin-2-yl]-benzoic acid;
4-[4-(3,4-methylenedioxyphenethylamino)-5-chloro-6-methyl-thieno-[2,3-d]-pyrimidin-2-yl]-benzoic acid;
4-[4-(3,4-methylenedioxyphenethylamino)-6-nitro-thieno-[2,3-d]-pyrimidin-2-yl]-benzoic acid;
4-[4-(3,4-methylenedioxyphenethylamino)-5,6-dimethyl-thieno-[2,3-d]-pyrimidin-2-yl]-benzoic acid;
4-[4-(3,4-methylenedioxyphenethylamino)-6-trifluoro-methyl-thieno-[2,3-d]-pyrimidin-2-yl]-benzoic acid;
4-[4-(3,4-ethylenedioxyphenethylamino)-6-methyl-thieno-[2,3-d]-pyrimidin-2-yl]-benzoic acid;
4-[4-(3,4-ethylenedioxyphenethylamino)-5-methyl-thieno-[2,3-d]-pyrimidin-2-yl]-benzoic acid;
4-[4-(3,4-ethylenedioxyphenethylamino)-5,6,7,8-tetrahydro-[1]-benzothieno-[2,3-d]-pyrimidin-2-yl]-benzoic acid;
4-[4-(3,4-ethylenedioxyphenethylamino)-5,6-cyclopenteno-thieno-[2,3-d]-pyrimidin-2-yl]-benzoic acid;
4-[4-(3,4-ethylenedioxyphenethylamino)-5,6-cyclohepteno-thieno-[2,3-d]-pyrimidin-2-yl]-benzoic acid;
4-[4-(3,4-ethylenedioxyphenethylamino)-6-ethyl-thieno-[2,3-d]-pyrimidin-2-yl]-benzoic acid;
4-[4-(3,4-ethylenedioxyphenethylamino)-6-chloro-thieno-[2,3-d]-pyrimidin-2-yl]-benzoic acid;
4-[4-(3,4-ethylenedioxyphenethylamino)-5-chloro-6-methyl-thieno-[2,3-d]-pyrimidin-2-yl]-benzoic acid;
4-[4-(3,4-ethylenedioxyphenethylamino)-6-nitro-thieno-[2,3-d]-pyrimidin-2-yl]-benzoic acid;
4-[4-(3,4-ethylenedioxyphenethylamino)-5,6-dimethyl-thieno-[2,3-d]-pyrimidin-2-yl]-benzoic acid;
4-[4-(3,4-ethylenedioxyphenethylamino)-6-trifluoro-methyl-thieno-[2,3-d]-pyrimidin-2-yl]-benzoic acid;
4-(4-phenethylamino-6-methyl-thieno-[2,3-d]-pyrimidin-2-yl)-benzoic acid;
4-(4-phenethylamino-5-methyl-thieno-[2,3-d]-pyrimidin-2-yl)-benzoic acid;
4-(4-phenethylamino-5,6,7,8-tetrahydro-[1]-benzothieno-[2,3-d]-pyrimidin-2-yl)-benzoic acid;
4-(4-phenethylamino-5,6-cyclopenteno-thieno-[2,3-d]-pyrimidin-2-yl)-benzoic acid;
4-(4-phenethylamino-5,6-cyclohepteno-thieno-[2,3-d]-pyrimidin-2-yl)-benzoic acid;
4-(4-phenethylamino-6-ethyl-thieno-[2,3-d]-pyrimidin-2-yl)-benzoic acid;
4-(4-phenethylamino-6-chloro-thieno-[2,3-d]-pyrimidin-2-yl)-benzoic acid;
4-(4-phenethylamino-5-chloro-6-methyl-thieno-[2,3-d]-pyrimidin-2-yl)-benzoic acid;
4-(4-phenethylamino-6-nitro-thieno-[2,3-d]-pyrimidin-2-yl)-benzoic acid;
4-(4-phenethylamino-5,6-dimethyl-thieno-[2,3-d]-pyrimidin-2-yl)-benzoic acid;
4-(4-phenethylamino-6-trifluoro-methyl-thieno-[2,3-d]-pyrimidin-2-yl)-benzoic acid,
are obtained.

Analogously to Example 5, using methyl 3-cyanobenzoate and subsequent hydrolysis, the compound 3-[4-(3,4-methylenedioxybenzylamino)-5,6,7,8-tetrahydro-[1]-benzothieno-[2,3-d]-pyrimidine-2-yl]-benzoic acid is obtained.

EXAMPLE 7

Analogously to Example 5 and 6, the following carboxylic acids are obtained using the corresponding 4-cyanocyclohexanecarboxylic acid esters
4-[4-(3,4-methylenedioxybenzylamino)-6-methyl-thieno-[2,3-d]-pyrimidin-2-yl]-cyclohexane-carboxylic acid;
4-[4-(3,4-methylenedioxybenzyl)-5-methyl-thieno-[2,3-d]-pyrimidin-2-yl]-cyclohexanecarboxylic acid;
4-[4-(3,4-methylenedioxybenzylamino)-5,6,7,8-tetrahydro-[1]-benzothieno-[2,3-d]-pyrimidin-2-yl]-cyclohexanecarboxylic acid, amorphous;
4-[4-(3,4-methylenedioxybenzylamino)-5,6-cyclopenteno-thieno-[2,3-d]-pyrimidin-2-yl]-cyclohexanecarboxylic acid;
4-[4-(3,4-methylenedioxybenzylamino)-5,6-cyclohepteno-thieno-[2,3-d]-pyrimidin-2-yl]-cyclohexanecarboxylic acid;
4-[4-(3,4-methylenedioxybenzylamino)-6-ethyl-thieno-[2,3-d]-pyrimidin-2-yl]-cyclohexanecarboxylic acid;
4-[4-(3,4-methylenedioxybenzylamino)-6-chloro-thieno-[2,3-d]-pyrimidin-2-yl]-cyclohexanecarboxylic acid;
4-[4-(3,4-methylenedioxybenzylamino)-5-chloro-6-methyl-thieno-[2,3-d]-pyrimidin-2-yl]-cyclohexanecarboxylic acid;
4-[4-(3,4-methylenedioxybenzylamino)-6-nitro-thieno-[2,3-d]-pyrimidin-2-yl]-cyclohexanecarboxylic acid;
4-[4-(3,4-methylenedioxybenzylamino)-5,6-dimethyl-thieno-[2,3-d]-pyrimidin-2-yl]-cyclohexanecarboxylic acid;
4-[4-(3,4-methylenedioxybenzylamino)-6-trifluoro-methyl-thieno-[2,3-d]-pyrimidin-2-yl]-cyclohexanecarboxylic acid;
4-[4-(3-chloro-methoxybenzylamino)-6-methyl-thieno-[2,3-d]-pyrimidin-2-yl]-cyclohexanecarboxylic acid;
4-[4-(3-chloro-4-methoxybenzylamino)-5-methyl-thieno-[2,3-d]-pyrimidin-2-yl]-cyclohexanecarboxylic acid;
4-[4-(3-chloro-4-methoxybenzylamino)-5,6,7,8-tetrahydro-[1]-benzothieno-[2,3-d]-pyrimidin-2-yl]-cyclohexanecarboxylic acid, amorphous;
4-[4-(3-chloro-4-methoxybenzylamino)-5,6-cyclo-penteno-thieno-[2,3-d]-pyrimidin-2-yl]-cyclohexanecarboxylic acid;
4-[4-(3-chloro-4-methoxybenzylamino)-5,6-cyclo-hepteno-thieno-[2,3-d]-pyrimidin-2-yl]-cyclohexanecarboxylic acid;
4-[4-(3-chloro-4-methoxybenzylamino)-6-ethyl-thieno-[2,3-d]-pyrimidin-2-yl]-cyclohexanecarboxylic acid;
4-[4-(3-chloro-4-methoxybenzylamino)-6-chloro-thieno-[2,3-d]-pyrimidin-2-yl]-cyclohexanecarboxylic acid;
4-[4-(3-chloro-4-methoxybenzylamino)-5-chloro-6-methyl-thieno-[2,3-d]-pyrimidin-2-yl]-cyclohexanecarboxylic acid;
4-[4-(3-chloro-4-methoxybenzylamino)-6-nitro-thieno-[2,3-d]-pyrimidin-2-yl]-cyclohexanecarboxylic acid;
4-[4-(3-chloro-4-methoxybenzylamino)-5,6-dimethyl-thieno-[2,3-d]-pyrimidin-2-yl]-cyclohexanecarboxylic acid;
4-[4-(3-chloro-4-methoxybenzylamino)-6-trifluoro-methyl-thieno-[2,3-d]-pyrimidin-2-yl]-cyclohexanecarboxylic acid;
4-[4-(3,4-dimethoxybenzylamino)-6-methyl-thieno-[2,3-d]-pyrimidin-2-yl]-cyclohexanecarboxylic acid;

4-[4-(3,4-dimethoxybenzylamino)-5-methyl-thieno-[2,3-d]-pyrimidin-2-yl]-cyclohexanecarboxylic acid;

4-[4-(3,4-dimethoxybenzylamino)-5,6,7,8-tetra-hydro-[1]-benzo-thieno-[2,3-d]-pyrimidin-2-yl]-cyclohexanecarboxylic acid;

4-[4-(3,4-dimethoxybenzylamino)-5,6-cyclopenteno-thieno-[2,3-d]-pyrimidin-2-yl]-cyclohexanecarboxylic acid;

4-[4-(3,4-dimethoxybenzylamino)-5,6-cyclohepteno-thieno-[2,3-d]-pyrimidin-2-yl]-cyclohexanecarboxylic acid;

4-[4-(3,4-dimethoxybenzylamino)-6-ethyl-thieno-[2,3-d]-pyrimidin-2-yl]-cyclohexanecarboxylic acid;

4-[4-(3,4-dimethoxybenzylamino)-6-chloro-thieno-[2,3-d]-pyrimidin-2-yl]-cyclohexanecarboxylic acid;

4-[4-(3,4-dimethoxybenzylamino)-5-chloro-6-methyl-thieno-[2,3-d]-pyrimidin-2-yl]-cyclohexanecarboxylic acid;

4-[4-(3,4-dimethoxybenzylamino)-6-nitro-thieno-[2,3-d]-pyrimidin-2-yl]-cyclohexanecarboxylic acid;

4-[4-(3,4-dimethoxybenzylamino)-5,6-dimethyl-thieno-[2,3-d]-pyrimidin-2-yl]-cyclohexanecarboxylic acid;

4-[4-(3,4-dimethoxybenzylamino)-6-trifluoromethyl-thieno-[2,3-d]-pyrimidin-2-yl]-cyclohexanecarboxylic acid;

4-(4-benzylamino-6-methyl-thieno-[2,3-d]-pyrimidin-2-yl)-cyclohexanecarboxylic acid;

4-(4-benzylamino-5-methyl-thieno-[2,3-d]-pyrimidin-2-yl)-cyclohexanecarboxylic acid;

4-(4-benzylamino-5,6,7,8-tetra-hydro-[1]-benzothieno-[2,3-d]-pyrimidin-2-yl)-cyclohexanecarboxylic acid, amorphous;

4-(4-benzylamino-5,6-cyclo-penteno-thieno-[2,3-d]-pyrimidin-2-yl)-cyclohexanecarboxylic acid;

4-(4-benzylamino-5,6-cyclohepteno-thieno-[2,3-d]-pyrimidin-2-yl)-cyclohexanecarboxylic acid;

4-(4-benzylamino-6-ethyl-thieno-[2,3-d]-pyrimidin-2-yl)-cyclohexanecarboxylic acid;

4-(4-benzylamino-6-chloro-thieno-[2,3-d]-pyrimidin-2-yl)-cyclohexanecarboxylic acid;

4-(4-benzylamino-5-chloro-6-methyl-thieno-[2,3-d]-pyrimidin-2-yl)-cyclohexanecarboxylic acid;

4-(4-benzylamino-6-nitro-thieno-[2,3-d]-pyrimidin-2-yl)-cyclohexanecarboxylic acid;

4-(4-benzylamino-5,6-dimethyl-thieno-[2,3-d]-pyrimidin-2-yl)-cyclohexanecarboxylic acid;

4-(4-benzylamino-6-trifluoromethyl-thieno-[2,3-d]-pyrimidin-2-yl)-cyclohexanecarboxylic acid;

4-[4-(4-fluorobenzylamino)-6-methyl-thieno-[2,3-d]-pyrimidin-2-yl]-cyclohexanecarboxylic acid;

4-[4-(4-fluorobenzylamino)-5-methyl-thieno-[2,3-d]-pyrimidin-2-yl]-cyclohexanecarboxylic acid;

4-[4-(4-fluorobenzylamino)-5,6,7,8-tetrahydro-[1]-benzothieno-[2,3-d]-pyrimidin-2-yl]-cyclohexanecarboxylic acid;

4-[4-(4-fluorobenzylamino)-5,6-cyclopenteno-thieno-[2,3-d]-pyrimidin-2-yl]-cyclohexanecarboxylic acid;

4-[4-(4-fluorobenzylamino)-5,6-cyclohepteno-thieno-[2,3-d]-pyrimidin-2-yl]-cyclohexanecarboxylic acid;

4-[4-(4-fluorobenzylamino)-6-ethyl-thieno-[2,3-d]-pyrimidin-2-yl]-cyclohexanecarboxylic acid; 4-[4-(4-fluorobenzylamino)-6-chloro-thieno-[2,3-d]-pyrimidin-2-yl]-cyclohexanecarboxylic acid;

4-[4-(4-fluorobenzylamino)-5-chloro-6-methyl-thieno-[2,3-d]-pyrimidin-2-yl]-cyclohexanecarboxylic acid;

4-[4-(4-fluorobenzylamino)-6-nitro-thieno-[2,3-d]-pyrimidin-2-yl]-cyclohexanecarboxylic acid;

4-[4-(4-fluorobenzylamino)-5,6-dimethyl-thieno-[2,3-d]-pyrimidin-2-yl]-cyclohexanecarboxylic acid;

4-[4-(4-fluorobenzylamino)-6-trifluoromethyl-thieno-[2,3-d]-pyrimidin-2-yl]-cyclohexane-carboxylic acid;

4-[4-(3,4-dichlorobenzylamino)-6-methyl-thieno-[2,3-d]-pyrimidin-2-yl]-cyclohexanecarboxylic acid;

4-[4-(3,4-dichlorobenzylamino)-5-methyl-thieno-[2,3-d]-pyrimidin-2-yl]-cyclohexanecarboxylic acid;

4-[4-(3,4-dichlorobenzylamino)-5,6,7,8-tetrahydro-[1]-benzothieno-[2,3-d]-pyrimidin-2-yl]-cyclohexanecarboxylic acid;

4-[4-(3,4-dichlorobenzylamino)-5,6-cyclopenteno-thieno-[2,3-d]-pyrimidin-2-yl]-cyclohexane-carboxylic acid;

4-[4-(3,4-dichlorobenzylamino)-5,6-cyclohepteno-thieno-[2,3-d]-pyrimidin-2-yl]-cyclohexanecarboxylic acid;

4-[4-(3,4-dichlorobenzylamino)-6-ethyl-thieno-[2,3-d]-pyrimidin-2-yl]-cyclohexanecarboxylic acid;

4-[4-(3,4-dichlorobenzylamino)-6-chloro-thieno-[2,3-d]-pyrimidin-2-yl]-cyclohexanecarboxylic acid;

4-[4-(3,4-dichlorobenzylamino)-5-chloro-6-methyl-thieno-[2,3-d]-pyrimidin-2-yl]-cyclohexanecarboxylic acid;

4-[4-(3,4-dichlorobenzylamino)-6-nitro-thieno-[2,3-d]-pyrimidin-2-yl]-cyclohexanecarboxylic acid;

4-[4-(3,4-dichlorobenzylamino)-5,6-dimethyl-thieno-[2,3-d]-pyrimidin-2-yl]-cyclohexanecarboxylic acid;

4-[4-(3,4-dichlorobenzylamino)-6-trifluoromethyl-thieno-[2,3-d]-pyrimidin-2-yl]-cyclohexanecarboxylic acid;

4-[4-(3-nitrobenzylamino)-6-methyl-thieno-[2,3-d]-pyrimidin-2-yl]-cyclohexanecarboxylic acid;

4-[4-(3-nitrobenzylamino)-5-methyl-thieno-[2,3-d]-pyrimidin-2-yl]-cyclohexanecarboxylic acid;

4-[4-(3-nitrobenzylamino)-5,6,7,8-tetrahydro-[1]-benzothieno-[2,3-d]-pyrimidin-2-yl]-cyclohexanecarboxylic acid;

4-[4-(3-nitrobenzylamino)-5,6-cyclopenteno-thieno-[2,3-d]-pyrimidin-2-yl]-cyclohexanecarboxylic acid;

4-[4-(3-nitrobenzylamino)-5,6-cyclohepteno-thieno-[2,3-d]-pyrimidin-2-yl]-cyclohexanecarboxylic acid;

4-[4-(3-nitrobenzylamino)-6-ethyl-thieno-[2,3-d]-pyrimidin-2-yl]-cyclohexanecarboxylic acid;

4-[4-(3-nitrobenzylamino)-6-chloro-thieno-[2,3-d]-pyrimidin-2-yl]-cyclohexanecarboxylic acid;

4-[4-(3-nitrobenzylamino)-5-chloro-6-methyl-thieno-[2,3-d]-pyrimidin-2-yl]-cyclohexanecarboxylic acid;

4-[4-(3-nitrobenzylamino)-6-nitro-thieno-[2,3-d]-pyrimidin-2-yl]-cyclohexanecarboxylic acid;

4-[4-(3-nitrobenzylamino)-5,6-dimethyl-thieno-[2,3-d]-pyrimidin-2-yl]-cyclohexanecarboxylic acid;

4-[4-(3-nitrobenzylamino)-6-trifluoromethyl-thieno-[2,3-d]-pyrimidin-2-yl]-cyclohexanecarboxylic acid;

4-[4-(3,4-methylenedioxyphenethylamino)-6-methyl-thieno-[2,3-d]-pyrimidin-2-yl]-cyclohexanecarboxylic acid;

4-[4-(3,4-methylenedioxyphenethylamino)-5-methyl-thieno-[2,3-d]-pyrimidin-2-yl]-cyclohexanecarboxylic acid;

4-[4-(3,4-methylenedioxyphenethylamino)-5,6,7,8-tetrahydro-[1]-benzothieno-[2,3-d]-pyrimidin-2-yl]-cyclohexanecarboxylic acid;

4-[4-(3,4-methylenedioxyphenethylamino)-5,6-cyclopenteno-thieno-[2,3-d]-pyrimidin-2-yl]-cyclohexanecarboxylic acid;

4-[4-(3,4-methylenedioxyphenethylamino)-5,6-cyclohepteno-thieno-[2,3-d]-pyrimidin-2-yl]-cyclohexanecarboxylic acid;

4-[4-(3,4-methylenedioxyphenethylamino)-6-ethyl-thieno-[2,3-d]-pyrimidin-2-yl]-cyclohexanecarboxylic acid;

4-[4-(3,4-methylenedioxyphenethylamino)-6-chloro-thieno-[2,3-d]-pyrimidin-2-yl]-cyclohexanecarboxylic acid;
4-[4-(3,4-methylenedioxyphenethylamino)-5-chloro-6-methyl-thieno-[2,3-d]-pyrimidin-2-yl]-cyclohexanecarboxylic acid;
4-[4-(3,4-methylenedioxyphenethylamino)-6-nitro-thieno-[2,3-d]-pyrimidin-2-yl]-cyclohexanecarboxylic acid;
4-[4-(3,4-methylenedioxyphenethylamino)-5,6-dimethyl-thieno-[2,3-d]-pyrimidin-2-yl]-cyclohexanecarboxylic acid;
4-[4-(3,4-methylenedioxyphenethylamino)-6-trifluoro-methyl-thieno-[2,3-d]-pyrimidin-2-yl]-cyclohexanecarboxylic acid;
4-[4-(3,4-ethylenedioxyphenethylamino)-6-methyl-thieno-[2,3-d]-pyrimidin-2-yl]-cyclohexanecarboxylic acid;
4-[4-(3,4-ethylenedioxyphenethylamino)-5-methyl-thieno-[2,3-d]-pyrimidin-2-yl]-cyclohexanecarboxylic acid;
4-[4-(3,4-ethylenedioxyphenethylamino)-5,6,7,8-tetrahydro-[1]-benzothieno-[2,3-d]-pyrimidin-2-yl]-cyclohexanecarboxylic acid;
4-[4-(3,4-ethylenedioxyphenethylamino)-5,6-cyclopenteno-thieno-[2,3-d]-pyrimidin-2-yl]-cyclohexanecarboxylic acid;
4-[4-(3,4-ethylenedioxyphenethylamino)-5,6-cyclohepteno-thieno-[2,3-d]-pyrimidin-2-yl]-cyclohexanecarboxylic acid;
4-[4-(3,4-ethylenedioxyphenethylamino)-6-ethyl-thieno-[2,3-d]-pyrimidin-2-yl]-cyclohexanecarboxylic acid;
4-[4-(3,4-ethylenedioxyphenethylamino)-6-chloro-thieno-[2,3-d]-pyrimidin-2-yl]-cyclohexanecarboxylic acid;
4-[4-(3,4-ethylenedioxyphenethylamino)-5-chloro-6-methyl-thieno-[2,3-d]-pyrimidin-2-yl]-cyclohexanecarboxylic acid;
4-[4-(3,4-ethylenedioxyphenethylamino)-6-nitro-thieno-[2,3-d]-pyrimidin-2-yl]-cyclohexanecarboxylic acid;
4-[4-(3,4-ethylenedioxyphenethylamino)-5,6-dimethyl-thieno-[2,3-d]-pyrimidin-2-yl]-cyclohexanecarboxylic acid;
4-[4-(3,4-ethylenedioxyphenethylamino)-6-trifluoro-methyl-thieno-[2,3-d]-pyrimidin-2-yl]-cyclohexanecarboxylic acid;
4-(4-phenethylamino-6-methyl-thieno-[2,3-d]-pyrimidin-2-yl)-cyclohexanecarboxylic acid;
4-(4-phenethylamino-5-methyl-thieno-[2,3-d]-pyrimidin-2-yl)-cyclohexanecarboxylic acid;
4-(4-phenethylamino-5,6,7,8-tetrahydro-[1]-benzo-thieno-[2,3-d]-pyrimidin-2-yl)-cyclohexanecarboxylic acid;
4-(4-phenethylamino-5,6-cyclopenteno-thieno-[2,3-d]-pyrimidin-2-yl)-cyclohexanecarboxylic acid;
4-(4-phenethylamino-5,6-cyclohepteno-thieno-[2,3-d]-pyrimidin-2-yl)-cyclohexanecarboxylic acid;
4-(4-phenethylamino-6-ethyl-thieno-[2,3-d]-pyrimidin-2-yl)-cyclohexanecarboxylic acid;
4-(3,4-phenethylamino-6-chloro-thieno-[2,3-d]-pyrimidin-2-yl)-cyclohexanecarboxylic acid;
4-(4-phenethylamino-5-chloro-6-methyl-thieno-[2,3-d]-pyrimidin-2-yl)-cyclohexanecarboxylic acid;
4-(4-phenethylamino-6-nitro-thieno-[2,3-d]-pyrimidin-2-yl)-cyclohexanecarboxylic acid;
4-(4-phenethylamino-5,6-dimethyl-thieno-[2,3-d]-pyrimidin-2-yl)-cyclohexanecarboxylic acid;
4-(4-phenethylamino-6-trifluoro-methyl-thieno-[2,3-d]-pyrimidin-2-yl)-cyclohexanecarboxylic acid,
are obtained.

EXAMPLE 8

A solution of 4-[4-(3-nitrobenzylamino)-5-methyl-thieno-[2,3-d]-pyrimidin-2-yl]-benzoic acid in methanol is hydrogenated in the presence of Raney nickel. The catalyst is filtered off and the solution is concentrated. After recrystallization, 4-[4-(3-amino-benzylamino)-5-methyl-thieno-[2,3-d]-pyrimidin-2-yl]-benzoic acid is obtained.

EXAMPLE 9

1 ml of freshly distilled acetaldehyde is added to a solution of 6 g of 4-[4-(3-aminobenzylamino)-5-methyl-thieno-[2,3-d]-pyrimidin-2-yl]-benzoic acid and 0.5 g of titanium tetrachloride in 100 ml of methanol. 4 g of sodium cyanoborohydride are then added and the mixture is stirred for 30 hours. Half-concentrated hydrochloric acid is added to the mixture, the mixture is worked up in the customary manner and 4-[4-(3-N-ethylaminobenzylamino)-5-methyl-thieno-[2,3-d]-pyrimidin-2-yl]-benzoic acid is obtained.

EXAMPLE 10

Analogously to Example 2, by reaction of 2-chloro-5,6,7,8-tetrahydro-4-(3,4-methylenedioxybenzylamino)-[1]-benzothieno-[2,3-d]-pyrimidine
with ethyl piperazin-1-yl-acetate
ethyl {4-[4-(3,4-methylenedioxybenzylamino)-5,6,7,8-tetrahydro-[1]-benzothieno-[2,3-d]-pyrimidin-2-yl]-piperazin-1-yl}-acetate
with ethyl piperidin-4-yl-acetate
ethyl {1-[4-(3,4-methylenedioxybenzylamino)-5,6,7,8-tetrahydro-[1]-benzothieno-[2,3-d]-pyrimidin-2-yl]-piperidin-1-yl}acetate
are obtained.
Ester hydrolysis of these compounds gives
{4-[4-(3,4-methylenedioxybenzylamino)-5,6,7,8-tetrahydro-[1]-benzothieno[2,3-d]-pyrimidin-2-yl]-piperazin-1-yl}acetic acid, m.p. 250° (decomposition) and {1-[4-(3,4-methylenedioxybenzylamino)-5,6,7,8-tetra-hydro-[1]-benzothieno-[2,3-d]-pyrimidin-2-yl]-piperidin-4-yl}acetic acid, amorphous.

EXAMPLE 11

Analogously to Examples 4 and 5 the following compounds are obtained:
ethyl {4-[4-(3,4-methylenedioxybenzylamino)-5,6,7,8-tetrahydro-[1]-benzothieno-[2,3-d]-pyrimidin-2-yl]-phenyl}-acetate and
ethyl {4-[4-(3-chloro-4-methoxybenzylamino)-5,6,7,8-tetrahydro-[1]-benzothieno-[2,3-d]-pyrimidin-2-yl]-phenyl}-acetate.
Ester hydrolysis of these compounds gives
{4-[4-(3,4-methylenedioxybenzylamino)-5,6,7,8-tetrahydro-[1]-benzothieno-[2,3-d]-pyrimidin-2-yl]-phenyl}acetic acid, m.p. 214° and
{4-[4-(3-chloro-4-methoxybenzylamino)-5,6,7,8-tetrahydro-[1]-benzothieno-[2,3-d]-pyrimidin-2-yl]-phenyl}acetic acid, sodium salt, m.p. >250°.
The following examples relate to pharmaceutical formulations:

EXAMPLE A

Injection vials

A solution of 100 g of an active compound of the formula I and 5 g of disodium hydrogen phosphate in 3 l of doubly distilled water is brought to pH 6.5 with 2N hydrochloric acid, and subjected to sterile filtration and injection bottles are filled with this solution, lyophilized under sterile conditions and closed under sterile conditions. Each injection vial contains 5 mg of active compound.

37

EXAMPLE B

Suppositories

A mixture of 20 g of an active compound of the formula I with 100 g of soyalecithin and 1400 g of cacao butter is melted, poured into moulds and allowed to cool. Each suppository comprises 20 mg of active compound.

EXAMPLE C

Solution

A solution of 1 g of an active compound of the formula I, 9.38 g of $NaH_2PO_4.2 H_2O$, 28.48 g of $Na_2HPO_4.12 H_2O$ and 0.1 g of benzalkonium chloride in 940 ml of doubly distilled water is prepared. The pH is brought to 6.8 and the solution is topped up to 1 l and sterilized by irradiation. This solution can be used in the form of eye drops.

EXAMPLE D

Ointment 500 mg of an active compound of the formula I are mixed with 99.5 g of vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed to tablets in the customary manner such that each tablet comprises 10 mg of active compound.

EXAMPLE F

Coated tablets

Tablets are pressed analogously to Example E and are then covered in the customary manner with a coating of sucrose, potato starch, talc, tragacanth and dyestuff.

EXAMPLE G

Capsules

Hard gelatin capsules are filled with 2 kg of active compound of the formula I in the customary manner such that each capsule contains 20 mg of the active compound.

EXAMPLE H

Ampoules

A solution of 1 kg of active compound of the formula I in 60 l of doubly distilled water is subjected to sterile filtration and ampoules are filled with the solution, lyophilized under sterile conditions and closed under sterile conditions. Each ampoule contains 10 mg of active compound.

EXAMPLE I

Spray for inhalation 14 g of active compound of the formula I are dissolved in 10 l of isotonic NaCl solution and commercially available spray vessels with a pump mechanism are filled with the solution. The solution can be sprayed into the mouth or nose. One spray puff (about 0.1 ml) corresponds to a dose of about 0.14 mg.

38

What is claimed is:
1. Compounds of the formula I

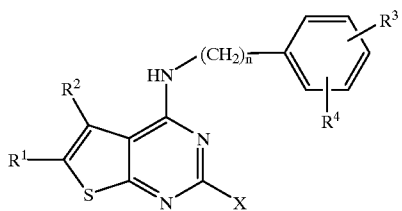

wherein
$R^1$, $R^2$ in each case independently of one another are H, A, OA, alkenyl, alkynyl, $CR_3$ or Hal, where one of the radicals $R^1$ or $R^2$ is always ≠H, $R^1$ and $R^2$ together are also alkylene having 3–5 C atoms, $R^3$, $R^4$ in each case independently of one another are H, A, OA, $NO_2$, $NH_2$ NHA, NAA' or Hal, $R^3$ and $R^4$ together also are —O—$CH_2$—$CH_2$—, —O—$CH_2$—O— or —O—$CH_2$—$CH_2$—O—, X is a 5- to 7-membered saturated heterocyclic ring which is mono- or disubstituted by $R^5$, or a 5- to 7-membered unsaturated or saturated isocyclic ring which is mono- or disubstituted by $R^5$, $R^5$ is COOH, COOA, $CONH_2$, CONAA', CONHA, CN, $CH_2COOH$ or $CH_2CH_2COOH$, A,A' in each case independently of one another are H or alkyl having 1 to 6 C atoms, Hal is F, Cl, Br or I
and
n is 0, 1, 2 or 3, and physiologically acceptable salts thereof.

2. Compounds of the formula I according to claim 1
(a) 4-[4-(3,4-methylenedioxy-benzylamino)-5,6,7,8-tetrahydro-[1]-benzothieno-[2,3-d]-pyrimidin-2-yl]-benzoic acid;
(b) 4-[4-(3,4-methylenedioxybenzylamino)-6-methyl-thieno-[2,3-d]-pyrimidin-2-yl]-benzoic acid;
(c) 4-[4-(3,4-methylenedioxy-benzylamino)-5,6-dimethyl-thieno-[2,3-d]-pyrimidin-2-yl]-benzoic acid;
(d) 4-[4-(3,4-methylenedioxybenzylamino)-6-chloro-thieno-[2,3-d]-pyrimidin-2-yl]-benzoic acid;
(e) 4-[4-(3-chloro-4-methoxy-benzylamino)-5,6,7,8-tetrahydro-[1]-benzothieno-[2,3-d]-pyrimidin-2-yl]-benzoic acid;
(f) 1-[4-(3,4-methylenedioxy-benzylamino)-5,6,7,8-tetrahydro-[1]-benzothieno-[2,3-d]-pyrimidin-2-yl]-piperidine-4-carboxylic acid;
(g) 1-[4-(3,4-methylenedioxy-benzylamino)-6-methyl-thieno-[2,3-d]-pyrimidin-2-yl]-piperidine-4-carboxylic acid;
(h) 4-[4-(3,4-methylenedioxy-benzylamino)-5,6,7,8-tetrahydro-[1]-benzothieno-[2,3-d]-pyrimidin-2-yl]-cyclohexanecarboxylic acid;
and physiologically acceptable salts thereof.

3. A process for the preparation
a) of compounds of the formula I according to claim 1, and salts thereof, wherein X is a saturated 5- to 7-membered heterocyclic ring which is mono- or disubstituted by $R^5$ and is bonded via N, characterized in that a compound of the formula II

II

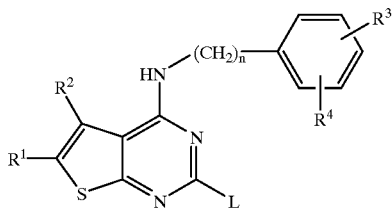

wherein
$R^1$, $R^2$, $R^3$, $R^4$ and n have the meanings given and L is Cl, Br, OH, $SCH_3$ or a reactive esterified OH group, is reacted with a saturated 5- to 7-membered heterocyclic ring which is mono- or disubstituted by $R^5$, wherein $R^5$ has the meaning given, or b) of compounds of the formula I according to claim 1, and salts thereof, wherein X is an unsaturated or saturated 5- to 7-membered isocyclic ring which is mono- or disubstituted by $R^5$ and is bonded via C, characterized in that a compound of the formula III

III

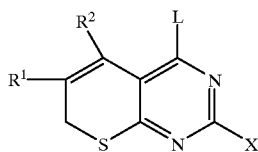

wherein
$R^1$, $R^2$ and X have the meanings given
and L is Cl, Br, OH, $SCH_3$ or a reactive esterified OH group, is reacted with a compound of the formula IV

IV

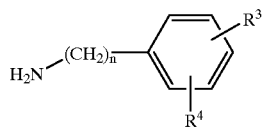

wherein
$R^3$, $R^4$ and n have the meanings given, or c) in a compound of the formula I, a radical $R^3$ and/or $R^4$ is converted into another radical $R^3$ or $R^4$ by reducing a nitro group, or a radical X is converted into another radical X by hydrolyzing an ester and/or in that an acid compound of the formula I is converted into one of its salts by treatment with a base.

4. Process for the preparation of pharmaceutical formulations, characterized in that a compound of the formula I according to claim 1 and/or one of its physiologically acceptable salts is brought into a suitable dosage form together with at least one solid, liquid or semi-liquid carrier or auxiliary.

5. Pharmaceutical formulation, characterized by a content of at least one compound of the formula I according to claim 1 and/or one of its physiologically acceptable salts.

6. A method for treating cardiovascular disease in a host in need thereof, comprising administering to said host an effective amount of a compound according to claim 1.

7. A method for treating erectile dysfunction in a host in a host in need thereof, comprising administering to said host an effective amount of a compound according to claim 1.

8. A method for inhibiting phosphodiesterase V activity, comprising administering an effective amount of a compound according to claim 1.

* * * * *